(12) United States Patent
Hanaoka et al.

(10) Patent No.: US 10,004,815 B2
(45) Date of Patent: Jun. 26, 2018

(54) NEAR-INFRARED QUENCHING GROUP

(71) Applicant: THE UNIVERSITY OF TOKYO, Tokyo (JP)

(72) Inventors: Kenjiro Hanaoka, Tokyo (JP); Takuya Myochin, Tokyo (JP); Tetsuo Nagano, Tokyo (JP); Yasuteru Urano, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days. days.

(21) Appl. No.: 15/035,593

(22) PCT Filed: Dec. 4, 2014

(86) PCT No.: PCT/JP2014/082140
§ 371 (c)(1),
(2) Date: Jun. 27, 2016

(87) PCT Pub. No.: WO2015/083799
PCT Pub. Date: Jun. 11, 2015

(65) Prior Publication Data
US 2016/0296639 A1    Oct. 13, 2016

(30) Foreign Application Priority Data
Dec. 4, 2013 (JP) .................. 2013-251279

(51) Int. Cl.
*C07F 7/08* (2006.01)
*A61K 49/00* (2006.01)

(52) U.S. Cl.
CPC .......... *A61K 49/0041* (2013.01); *C07F 7/083* (2013.01); *C07F 7/0812* (2013.01); *C07F 7/0816* (2013.01)

(58) Field of Classification Search
CPC .................................................. C07F 7/0812
See application file for complete search history.

(56) References Cited

U.S. PATENT DOCUMENTS

| 6,399,392 B1 | 6/2002 | Haugland et al. |
| 2014/0140930 A1 | 5/2014 | Bogyo et al. |
| 2014/0314677 A1 | 10/2014 | Groves et al. |

FOREIGN PATENT DOCUMENTS

| JP | 5526124 B2 | 6/2014 |
| WO | 00/64988 A1 | 11/2000 |
| WO | 2010/126077 A1 | 11/2010 |
| WO | 2012/111818 A1 | 8/2012 |
| WO | 2012/118715 A2 | 9/2012 |
| WO | 2014/144793 A1 | 9/2014 |

OTHER PUBLICATIONS

Fu et al., "A design concept of long-wavelength fluorescent analogs of rhodamine dyes: replacement of oxygen with silicon atom", Chemical Communications, 2008, pp. 1780-1782, (15).
Grimm et al., "Carbofluoresceins and Carborhodamines as Scaffolds for High-Contrast Fluorogenic Probes", ACS Chemical Biology, 2013, pp. 1303-1310, 8 (6).
Koide et al., "Development of NIR Fluorescent Dyes Based on Si-rhodamine for in Vivo Imaging", Journal of the American Chemical Society, 2012, pp. 5029-5031, 134, (11).
Wang et al., "Spirolactonized Si-rhodamine: a novel NIR fluorophore utilized as a platform to construct Si-rhodamine-based probes", Chemical Communications, 2012, pp. 8781-8783, 48, (70).
International Search Report issued with respect to application No. PCT/JP2014/082140, dated Mar. 3, 2015.
International Preliminary Report on Patentability issued with respect to application No. PCT/JP2014/082140, dated Jun. 7, 2016.

*Primary Examiner* — Shawquia Jackson
(74) *Attorney, Agent, or Firm* — Greenblum & Bernstein, P.L.C.

(57) ABSTRACT

[Problem] To provide a novel near-infrared quencher.
[Solution] A compound represented by general formula (I) or a salt thereof.

15 Claims, 7 Drawing Sheets

NEAR-INFRARED QUENCHING GROUP

TECHNICAL FIELD

The present invention relates to a novel near-infrared fluorescent compound, a method for producing the same, and a fluorescent probe that uses this compound.

BACKGROUND ART

Observing various events in real time and at high sensitivity in vivo is extremely important for explaining biological phenomena. One means that has drawn attention in recent years is near-infrared fluorescent imaging using the near-infrared light region from 650 to 900 nm, which is a wavelength region suited to observation in vivo. This means is presumed to be attractive because the equipment is very simple, and the safety is high since no radioactive substances are used. The development of near-infrared fluorescent probes to be used in near-infrared fluorescent imaging is therefore an active research topic.

However, the development of fluorescent probes in the near-infrared light region is less adequate than fluorescent probes of the visible light region. This is due to a lack of useful fluorescence control principles in the near-infrared fluorescence region. FRET, one widely used fluorescence control principle, is an effective fluorescence control method in the near-infrared light region as well, and many near-infrared fluorescent probes that utilize it are being developed. In particular, the fact that the utilization of a non-fluorescent quencher as a FRET acceptor can raise the S/N ratio is leading to the development of useful probes.

However, there are also limitations to the development of FRET-type probes since there are no useful quenchers of the near-infrared light region even when FRET is used as a control mechanism. It would therefore be very useful in the evolution of the life sciences to develop quenchers in the near-infrared light region and to develop a variety of near-infrared fluorescent probes by utilizing them.

In the case of rhodamine which has absorption and fluorescence wavelengths in the visible light region, the fluorescence of rhodamine is known to be quenched and the wavelength lengthened by bonding a phenyl group and a derivative thereof to the nitrogen atoms at positions 3 and 6 (Patent Reference 1). Such non-fluorescent xanthene-type compounds are widely used as quenchers. However, their absorption wavelength is not reached until the second half of 700 nm. They are consequently unsuitable as quenchers of fluorophores such as Cy7, Cy7.5, and ICG which are common near-infrared fluorophores.

Thus, near-infrared quenchers that can be used as the scaffold structure of fluorescent probes in the near-infrared light region have not yet been developed.

PRIOR ART REFERENCES

Patent References

Patent Reference 1: International Publication WO 00/64988

SUMMARY OF THE INVENTION

Problems to be Solved by the Invention

The purpose of the present invention is to provide a novel near-infrared quencher. More specifically, the problem of the invention is to provide a novel compound wherein the oxygen atom at position 10 of the xanthene ring moiety of rhodamine is substituted by a silicon atom, a method for producing this compound, and a fluorescent probe utilizing this compound.

Means Used to Solve the Above-Mentioned Problems

The present inventors conducted studies intended to further lengthen the wavelength and develop quenchers capable of quenching common near-infrared fluorophores by substituting the oxygen atom at position 10 of the xanthene ring moiety by a silicon atom in a compound having a rhodamine skeleton with a phenyl group and derivative thereof bonded to the nitrogen atoms at positions 3 and 6 of rhodamine. As a result, a gradual decrease in absorption was observed in water even though it was possible to achieve non-fluorescence while lengthening the wavelength. They have made studies in order to solve this problem and discovered that introducing substituents at specific positions of the benzene ring bonded to position 9 of the xanthene ring can improve the stability of the compound in water and the compound has an adequate absorption wavelength as a quencher of the near-infrared light region, and thereby the present invention has been accomplished.

Specifically, the present invention relates to the following.

[1] A compound represented by general formula (I):

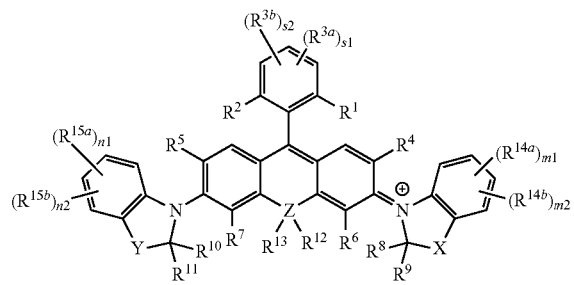

(in the formula,
$R^1$, $R^2$ each independently represent a C1-C6 alkyl group or C1-C6 alkoxy group;
$R^{3a}$ represents a monovalent substituent present on a benzene ring;
$R^{3b}$ represents a substituent capable of bonding with a fluorescent dye via a linker, when present;
$R^4$, $R^5$, $R^6$, and $R^7$ each independently represent a hydrogen atom, C1-C6 alkyl group, or halogen atom;
$R^8$, $R^9$, $R^{10}$, and $R^{11}$ each independently represent a hydrogen atom, C1-C6 alkyl group, hydroxyl group, or halogen atom;
$R^{12}$ and $R^{13}$ each independently represent a C1-C6 alkyl group or aryl group;
$R^{14a}$ and $R^{15a}$ each independently represent a C1-C6 alkyl group or halogen atom;
$R^{14b}$ and $R^{15b}$ each independently represent an alkoxy group, alkylamino group, sulfone group, phosphoric acid group, or carboxyl group;
X and Y each independently represent —C($R^{16}$)($R^{17}$)—, —C($R^{18}$)($R^{19}$)—C($R^{20}$)($R^{21}$)—, or —C($R^{22}$)=C($R^{23}$)— (in the formulas, $R^{16}$, $R^{17}$, $R^{18}$, $R^{19}$, $R^{20}$, $R^{21}$, $R^{22}$, and $R^{23}$ each independently represent a hydrogen atom, C1-C6 alkyl group, hydroxyl group or halogen atom);

Z represents a silicon atom, germanium atom, carbon atom, or tin atom;

m1 and m2 each independently are an integer of 0-4, and m1+m2 is 4 or less;

n1 and n2 each independently are an integer of 0-4, and n1+n2 is 4 or less;

s1 and s2 each independently are an integer of 0-3, and s1+s2 is 3 or less), or a salt thereof.

[2] A compound according to [1] wherein m2 and n2 are each independently 1 or higher, or a salt thereof.

[3] A compound according to [1] or [2] wherein s2 is 1 or higher, or a salt thereof.

[4] A method for producing a compound represented by general formula (I) (in the formula, $R^1$-$R^{15b}$, X, Y, Z, m1, m2, n1, n2, s1, and s2 are as defined above)

(I)

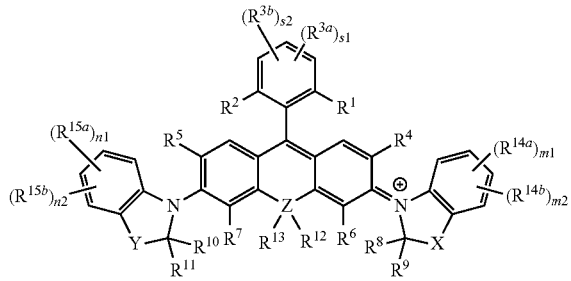

wherein the method comprises the following step of:

(a) obtaining a compound represented by general formula (III) (in the formula $R^4$-$R^7$, $R^{12}$, and $R^{13}$ are as defined in general formula (I)) by reacting a compound represented by general formula (II) (in the formula, $R^4$-$R^7$, $R^{12}$, and $R^{13}$ are as defined in general formula (I)) with sodium nitrite and potassium iodide under acidic conditions.

(II)

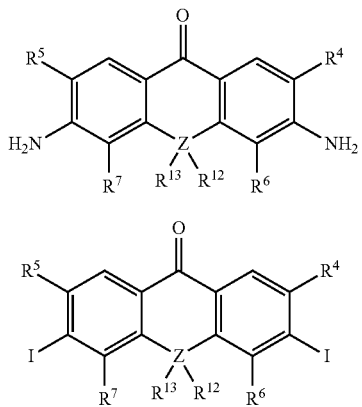

(III)

[5] A production method according to [4] comprising, after the step (a), the following steps of:

(b-1) obtaining a compound represented by general formula (V) (in the formula, $R^4$-$R^{13}$, $R^{14a}$, $R^{15a}$, m1, and n1 are as defined in general formula (I)) by reacting the compound of general formula (III) with a compound represented by general formula (IVa) (in the formula, $R^8$, $R^9$, $R^{14a}$, X, and m1 are as defined in general formula (I)) and a compound represented by general formula (IVb) (in the formula, $R^{10}$, $R^{11}$, $R^{15a}$, Y, and n1 are as defined in general formula (I)) in the presence of palladium acetate and BINAP;

(IVa)

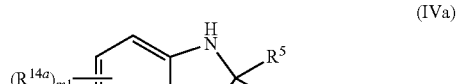

(IVb)

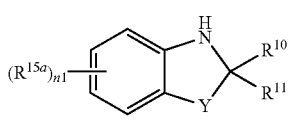

(V)

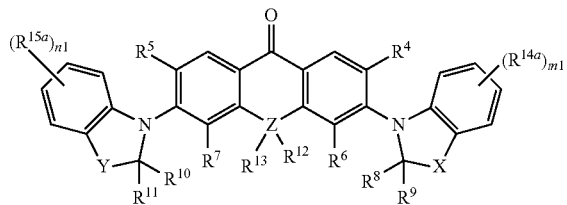

(c) obtaining a compound represented by general formula (VI) (in the formula, $R^4$-$R^{14a}$, $R^{15a}$, m1, m2, n1, and n2 are as defined in general formula (I), and $R^{14b}$, $R^{15b}$ are sulfone groups) by reacting the compound of general formula (V) with chlorosulfonic acid;

(VI)

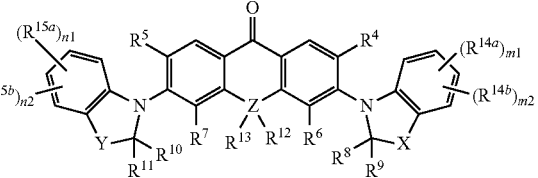

(d) obtaining a compound represented by general formula (VIa) (in the formula, $R^4$-$R^{13}$, $R^{14a}$ and $R^{15a}$, m1, m2, n1, and n2 are as defined in general formula (I), and ($R^{14b'}$-L) and ($R^{15b'}$-L) are groups of $R^{14b}$ and $R^{15b}$ protected by a protecting group L, respectively) by reacting the compound of general formula (VI) with a protecting reagent;

(VIa)

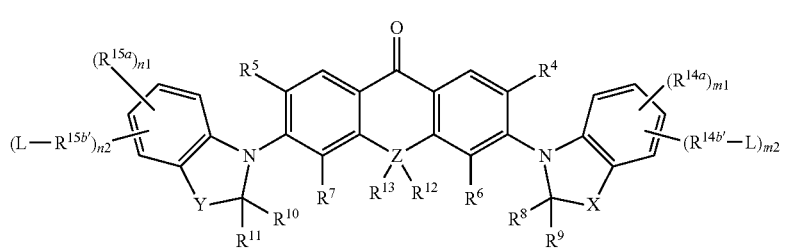

(e-1) obtaining a compound represented by general formula (I) (where, m2 and n2 are 1 or greater, $R^{14b}$, $R^{15b}$ are sulfone groups) by reacting the compound of general formula (VIa) with a compound represented by general formula (VII) (in the formula $R^1$-$R^{3b}$, s1, and s2 are as defined in general formula (I), and M, when present, is a protecting group of $R^{3b}$), and then eliminating the protecting group L and, when M is present in formula (VII), eliminating the protecting group M.

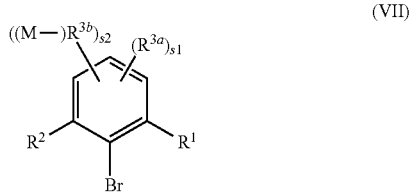

(VII)

[6] The method according to [4] comprising, after the step (a), the following steps of:

(b-2) obtaining a compound represented by general formula (Va) (in the formula, $R^4$-$R^{13}$, $R^{14a}$, $R^{15a}$, m1, and n1 are as defined in general formula (I), and U and V are as defined in general formulas (IVc) and (IVd), respectively) by reacting the compound of general formula (III) with a compound represented by general formula (IVc) (in the formula, $R^8$, $R^9$, $R^{14a}$, and m1 are as defined in general formula (I), and U represents $R^{14b}$ or a substituent that can be converted into $R^{14b}$) and a compound represented by general formula (IVd) (in the formula, $R^{10}$, $R^{11}$, $R^{15a}$, and n1 are as defined in general formula (I), and V represents $R^{15b}$ or a substituent that can be converted into $R^{15b}$) in the presence of a palladium catalyst such as palladium acetate and BINAP;

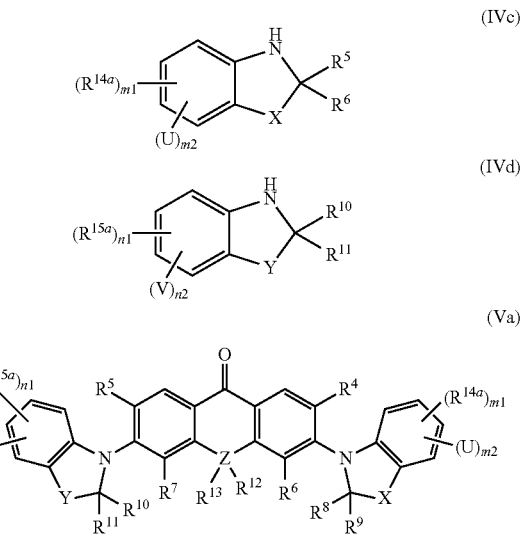

(e-2) obtaining a compound represented by general formula (I) (where, m2 and n2 are 1 or higher) by reacting the compound of general formula (Va) with a compound represented by general formula (VII) (in the formula, $R^1$-$R^{3b}$, s1, and s2 are as defined in general formula (I), and M, when present, is a protecting group of $R^{3b}$), and then eliminating the protecting group M when M is present in formula (VII), wherein when U and V, respectively, are a substituent that can be converted into $R^{14b}$ and a substituent that can be converted into $R^{15b}$, the method may comprise a step of converting U and V, respectively, into $R^{14b}$ and $R^{15b}$ before, during, or after step (e-2).

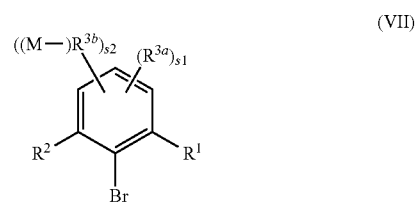

(VII)

[7] The method according to [4] comprising, after the step (a), the following steps of:

(b-1) obtaining a compound represented by general formula (V) (in the formula, $R^4$-$R^{13}$, $R^{14a}$, $R^{15a}$, m1, and n1 are as defined in general formula (I)) by reacting the compound of general formula (III) with a compound represented by general formula (IVa) (in the formula, $R^8$, $R^9$, $R^{14a}$, and m1 are as defined in general formula (I)) and a compound represented by general formula (IVb) (in the formula, $R^{10}$, $R^{11}$, $R^{15a}$, and n1 are as defined in general formula (I)) in the presence of a palladium catalyst such as palladium acetate and BINAP;

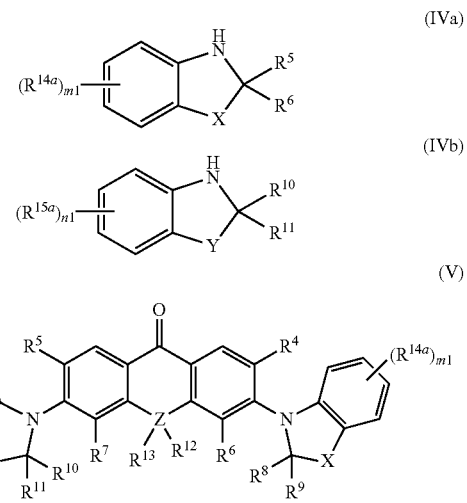

(e-3) obtaining a compound represented by general formula (I) (where, n1 and n2 are 0) by reacting the compound of general formula (V) with a compound represented by general formula (VII) (in the formula, $R^1$-$R^{3b}$, s1, and s2 are as defined in general formula (I), and M, when present, is a protecting group of $R^{3b}$), and then eliminating the protecting group M when M is present in formula (VII).

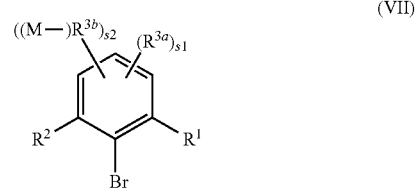

(VII)

[8] A fluorescent probe capable of detecting protons, metal ions, active oxygen species, enzymes, or low-oxygen environments, or the like, wherein the fluorescent probe comprises a residue of the compound according to any one of [1]-[3].

[9] A fluorescent labeling reagent wherein the fluorescent labeling reagent comprises a residue of the compound according to any one of [1]-[3].

[10] A fluorescent probe comprising a compound having a structure wherein a residue of the compound according to any one of [1]-[3] is bonded with a fluorescent dye, via a linker when present.

Advantages of the Invention

Compounds of the present invention are non-fluorescent in aqueous environments, having an absorption wavelength in the region up to 650-900 nm, and are also stable in water. Since the compounds of the present invention are therefore useful as near-infrared quenchers, they can be applied in near-infrared fluorescent imaging.

MODE FOR CARRYING OUT THE INVENTION

Figure 1:
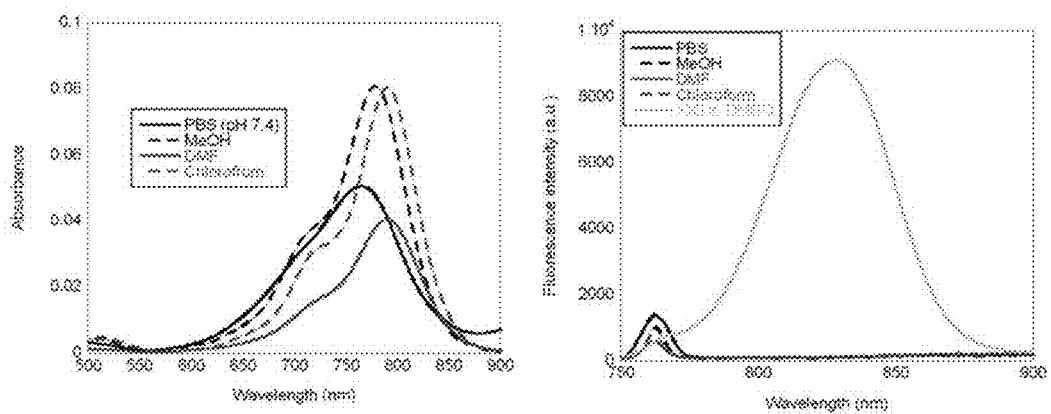
FIG. 1 Absorption spectrum and fluorescence spectrum of 2-Me-Si-QSY21 (comparative compound 1)

In this specification, an "alkyl group" or an alkyl moiety of a substituent containing an alkyl moiety (for example, an alkoxy group or the like), unless particularly stated otherwise, means a linear, branched, or cyclic alkyl group, or an alkyl group comprising a combination of these having, for example, 1-6 carbon atoms, preferably 1-4 carbon atoms, more preferably 1-3 carbon atoms. More specific examples of alkyl groups include a methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, or the like.

When "halogen atom" is used in this specification, it may be any of a fluorine atom, chlorine atom, bromine atom, or iodine atom, preferably a fluorine atom, chlorine atom, or bromine atom.

When "aryl group" is used in this specification, it means a monocyclic or polycyclic aromatic group; however, an aryl group may have one or more hetero atoms (for example, an oxygen atom, nitrogen atom, sulfur atom, or the like) as ring constituent atoms. When it has two or more hetero atoms, they may be the same or different. A phenyl group can preferably be used as an aryl group.

When certain functional groups are defined as "optionally substituted" in this specification, the type of substituent, substitution position, and number of substituents are not particularly restricted. When there are two or more substituents, they may be the same or different. Examples of substituents include, but are not limited to, an alkyl group, alkoxy group, hydroxyl group, carboxyl group, halogen atom, sulfo group, amino group, alkoxycarbonyl group, oxo group, and the like. Further substituents may be present in these substituents. Examples of such cases include, but are not limited to, an alkyl halide group, dialkylamino group, and the like.

One embodiment of the present invention is a compound represented by general formula (I) or a salt thereof.

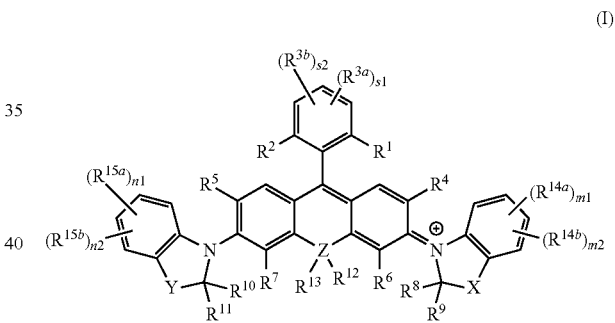

(I)

In formula (I), $R^1$, $R^2$ each independently represent a C1-C6 alkyl group or C1-C6 alkoxy group. When $R^1$ and $R^2$ represent alkyl groups, one or more halogen atoms, carboxyl groups, sulfonyl groups, hydroxyl groups, amino groups, alkoxy groups, and the like may be present in the alkyl group. A methyl group, methoxy group, isopropyl group, and butyl group are preferred as $R^1$, $R^2$. $R^1$ and $R^2$ may also be the same or different.

It is important in the present invention to have substituents at both ortho positions of the benzene ring bonded to position 9 of the xanthene ring (that is, position 2 and position 6 of the benzene ring). Compounds that do not have substituents at both ortho positions of this benzene ring were confirmed to have a gradual decrease in absorption in water even though they have an adequate absorption wavelength as a quencher of the near-infrared light region. While not wishing to be bound by theory, this is thought to be because a nucleophilic addition reaction of a water molecule to position 9 of the xanthene ring occurs, and the introduction of substituents at both ortho positions of the benzene ring suppresses nucleophilic attack to position 9 of the xanthene ring and makes it possible to improve the stability of the compound in water.

The type of monovalent substituent represented by $R^{3a}$ is not particularly restricted, but it is preferably selected, for example, from the group consisting of a C1-C6 alkyl group, C1-C6 alkenyl group, C1-C6 alkynyl group, C1-C6 alkoxy group, hydroxyl group, carboxy group, sulfonyl group, alkoxycarbonyl group, halogen atom, or amino group. These monovalent substituents may also have one or more arbitrary substituents. For example, one or more halogen atoms, carboxy groups, sulfonyl groups, hydroxyl groups, amino groups, alkoxy groups, or the like may be present in an alkyl group represented by $R^{3a}$; for example, an alkyl group indicated by $R^{3a}$ may be an alkyl halide group, hydroxyalkyl group, carboxyalkyl group, aminoalkyl group, or the like. In addition, for example, one or more alkyl groups may be present in an amino group represented by $R^{3a}$; an amino group represented by $R^{3a}$ may be a monoalkylamino group or a dialkylamino group. Furthermore, examples of when an alkoxy group represented by $R^{3a}$ has substituents include carboxy-substituted alkoxy groups, alkoxycarbonyl-substituted alkoxy groups, and the like; more specific examples include a 4-carboxybutoxy group, 4-acetoxymethyloxycarbonylbutoxy group, and the like.

In formula (I), s1 is an integer of 0-3. When s1 is 2 or higher, $R^{3a}$ may be the same or different. However, s1+s2 is 3 or less.

In formula (I), $R^{3b}$ represents a substituent that can bond with a fluorescent group via a linker, when present. In addition, s2 is an integer of 0-3. When s2 is 2 or higher, $R^{3b}$ may be the same or different. However, s1+s2 is 3 or less.

As will be described later, compounds of the present invention represented by general formula (I) or salts thereof are extremely useful as a scaffold structure of a fluorescent probe for specifically measuring protons, metal ions, active oxygen species, enzymes, low-oxygen environments, and the like (these are sometimes referred to as "objects of measurement") or as a scaffold structure of a fluorescent labeling reagent for fluorescent labeling of biological components. Therefore, in one aspect of the present invention, s2 in general formula (I) is preferably 1 or higher and the compound has at least one substituent that can bond with a fluorescent group via a linker, when present. Such substituents are preferably selected from a hydroxyl group, carboxy group, sulfonyl group, alkoxycarbonyl group, isothiocyanate group, or amino group. A fluorescent group can be introduced easily into the compound of the present invention if the compound of general formula (I) has at least one such substituent. Furthermore, the substitution position on the benzene ring of the substituent capable of bonding with a fluorescent group via a linker, when present, may be any position.

In general formula (I), $R^4$, $R^5$, $R^6$, and $R^7$ each independently represent a hydrogen atom, C1-C6 alkyl group, or halogen atom. When $R^4$, $R^5$, $R^6$, or $R^7$ represent an alkyl group, one or more halogen atoms, carboxy groups, sulfonyl groups, hydroxyl groups, amino groups, alkoxy groups, or the like may be present in the alkyl group. For example, an alkyl group represented by $R^4$, $R^5$, $R^6$, and $R^7$ may be an alkyl halide group, hydroxyalkyl group, carboxyalkyl group, or the like.

$R^4$ and $R^5$ are preferably each independently a hydrogen atom or halogen atom. More preferably, $R^4$ and $R^5$ are both hydrogen atoms, or $R^4$ and $R^5$ are both chlorine atoms or fluorine atoms.

$R^6$ and $R^7$ are preferably each independently a hydrogen atom or halogen atom. More preferably, $R^6$ and $R^7$ are both hydrogen atoms, or $R^6$ and $R^7$ are both chlorine atoms or fluorine atoms.

$R^8$, $R^9$, $R^{10}$, and $R^{11}$ each independently represent a hydrogen atom, C1-C6 alkyl group, hydroxyl group, or halogen atom. When $R^8$, $R^9$, $R^{10}$, and $R^{11}$ are alkyl groups, the alkyl group may be either unsubstituted or may have substituents. Optionally substituted alkyl groups are the same as explained for $R^3$. For example, $R^8$, $R^9$, $R^{10}$, and $R^{11}$ are preferably all hydrogen atoms, but it is also preferred if one or more of $R^8$, $R^9$, $R^{10}$, and $R^{11}$ is a hydrogen atom and the remainder are alkyl groups having 1-6 carbon atoms, hydroxyl groups, or chlorine atoms or other such halogen atoms.

In general formula (I), $R^{12}$ and $R^{13}$ each independently represent a C1-C6 alkyl group or aryl group. However, $R^{12}$ and $R^{13}$ are preferably each independently an alkyl group having 1-3 carbon atoms, and $R^{12}$ and $R^{13}$ are both more preferably methyl groups. One or more halogen atoms, carboxy groups, sulfonyl groups, hydroxyl groups, amino groups, alkoxy groups, or the like may be present in an alkyl group represented by $R^{12}$ and $R^{13}$. For example, an alkyl group represented by $R^{12}$ and $R^{13}$ may be an alkyl halide group, hydroxyalkyl group, carboxyalkyl group, or the like. When $R^{12}$ or $R^{13}$ represents an aryl group, the aryl group may be either a monocyclic aromatic group or a fused aromatic group, and the aryl ring may contain one or more ring constituent hetero atoms (for example, a nitrogen atom, sulfur atom, oxygen atom, or the like). A phenyl group is preferred as an aryl group. One or more substituents may be present on the aryl ring. For example, one or more halogen atoms, carboxy groups, sulfonyl groups, hydroxyl groups, amino groups, alkoxy groups, or the like may be present as substituents.

$R^{14a}$ and $R^{15a}$ each independently represent a C1-C6 alkyl group or a halogen atom. One or more halogen atoms, carboxy groups, sulfonyl groups, hydroxyl groups, amino groups, alkoxy groups, or the like may be present in an alkyl group represented by $R^{14a}$ and $R^{15a}$. For example, an alkyl group represented by $R^{14a}$ and $R^{15a}$ may be an alkyl halide group, hydroxyalkyl group, carboxyalkyl group, aminoalkyl group, or the like.

$R^{14b}$ and $R^{15b}$ each independently represent an alkoxy group, alkylamino group, sulfone group, phosphoric acid group, or carboxyl group.

In general formula (I), m1 and m2 each independently are an integer of 0-4. However, m1+m2 is 4 or less. When m1 is 2 or higher, $R^{14a}$ may be the same or different. When m2 is 2 or higher, $R^{14b}$ may be the same or different.

In general formula (I), n1 and n2 each independently are an integer of 0-4. However, n1+n2 is 4 or less. When n1 is 2 or higher, $R^{15a}$ may be the same or different. When n2 is 2 or higher, $R^{15b}$ may be the same or different.

The introduction of an alkoxy group, alkylamino group, sulfone group, phosphoric acid group, or carboxyl group as $R^{14b}$, $R^{15b}$ in a compound of general formula (I) is preferred because this makes it possible to raise the water solubility of the compound of general formula (I) and to use the compound as a water-soluble fluorescent probe. Therefore, one preferred embodiment of the present invention is a compound represented by general formula (I) wherein m2 and n2 are each independently 1 or higher, or a salt thereof.

In a more preferred embodiment of the present invention, m2 and n2 are an integer of 1 or higher and at least one combination of $R^{14b}$ and $R^{15b}$ is an alkoxy group, alkylamino group, sulfone group, phosphoric acid group, or carboxyl group.

In general formula (I), X and Y each independently represent —C($R^{16}$)($R^{17}$)—, —C($R^{18}$)($R^{19}$)—C($R^{20}$)($R^{21}$)—, or —C($R^{22}$)=C($R^{23}$)—. Here, $R^{16}$, $R^{17}$, $R^{18}$, $R^{19}$, $R^{20}$, $R^{21}$, $R^{22}$, and $R^{23}$ each independently represent a hydrogen atom, C1-C6 alkyl group, hydroxyl group, or halogen atom. When $R^{16}$, $R^{17}$, $R^{18}$, $R^{19}$, $R^{20}$, $R^{21}$, $R^{22}$, or $R^{23}$ is an alkyl group, the alkyl group may be unsubstituted or may have substituents. Optionally substituted alkyl groups are the same as explained for $R^3$.

In general formula (I), Z represents a silicon atom, germanium atom, carbon atom, or tin atom. Z is preferably a silicon atom or germanium atom, especially a silicon atom.

As described above, the substitution of the oxygen atom at position 10 of the xanthene ring moiety of the rhodamine skeleton by a silicon atom or the like and the introduction of substituents at both ortho positions of the benzene ring bonded to position 9 of the xanthene ring are major characteristics of the present invention, and could have been conceived of from the prior art. Specifically, while not wishing to be bound by theory, the xanthene ring is relatively stable since the lowest occupied molecular orbit (LUMO) energy level of the xanthene ring is relatively high in a rhodamine compound in which position 10 of the xanthene ring moiety is an oxygen atom. However, when the oxygen atom at position 10 of the xanthene ring is substituted by a silicon atom, the LUMO energy level of the xanthene ring becomes lower than the LUMO energy level of the xanthene ring of rhodamine containing an oxygen atom. Position 9 of the xanthene having a high LUMO coefficient becomes more susceptible to nucleophilic attack, undergoes a nucleophilic addition reaction by water molecules, and cleavage of the conjugation of the xanthene ring is facilitated. Thus, the present invention solves problems created by substituting the oxygen atom at position 10 of the xanthene ring moiety of the rhodamine skeleton by a silicon atom or the like by controlling the molecular structure of the benzene ring bonded to position 9 of the xanthene ring.

A compound represented by general formula (I) may have a counterion X appropriate for forming a quaternary ammonium salt. Examples of the counterion include, but are not limited to, a halogen ion, cyanide ion, acetate ion, trifluoroacetate ion, or the like. A compound represented by general formula (I) may form an intramolecular counterion with a quaternary nitrogen cation and an acidic group (for example, a carboxyl group or sulfo group) present in the molecule, or the like. Compounds represented by general formula (I) can also exist in the form of a salt. Examples of base addition salts can include a sodium salt, potassium salt, calcium salt, magnesium salt, or other such metal salt, ammonium salt, or triethylamine salt or other such organic amine salts, or the like. Examples of acid addition salts include hydrochlorides, sulfates, nitrates, and other such mineral acid salts, p-toluenesulfonates, methanesulfonates, maleates, oxalates, and other such organic acid salts. In addition to these, salts can also form with amino acids such as glycine or the like. Compounds represented by general formula (I) or salts thereof can also sometimes exist as hydrates or solvates, but all of these substances are encompassed within the scope of the present invention.

Compounds represented by general formula (I) can have one or more asymmetric carbons, depending on the types of substituents. Optically active compounds based on one or more asymmetric carbons and stereoisomers such as diastereomers based on two or more asymmetric carbons as well as arbitrary mixtures of stereoisomers, racemic compounds, and the like are all encompassed within the scope of the present invention.

Method for Synthesizing Compounds of the Present Invention

Compounds of general formula (I) of the present invention can be synthesized, for example, by the following methods. Here, compounds in which m2 and n2 are 1 or higher in general formula (I) can be synthesized by synthesis scheme 1, and compounds in which m2 and n2 are 0 (also referred to as compounds (Ia)) can be synthesized by synthesis scheme 2. Furthermore, in the following synthesis methods, $R^8$ and $R^{10}$, $R^9$ and $R^{11}$, X and Y, $R^{14a}$ and $R^{15a}$, $R^{14a}$ and $R^{15b}$, m1 and n1 in general formula (I) are the same.

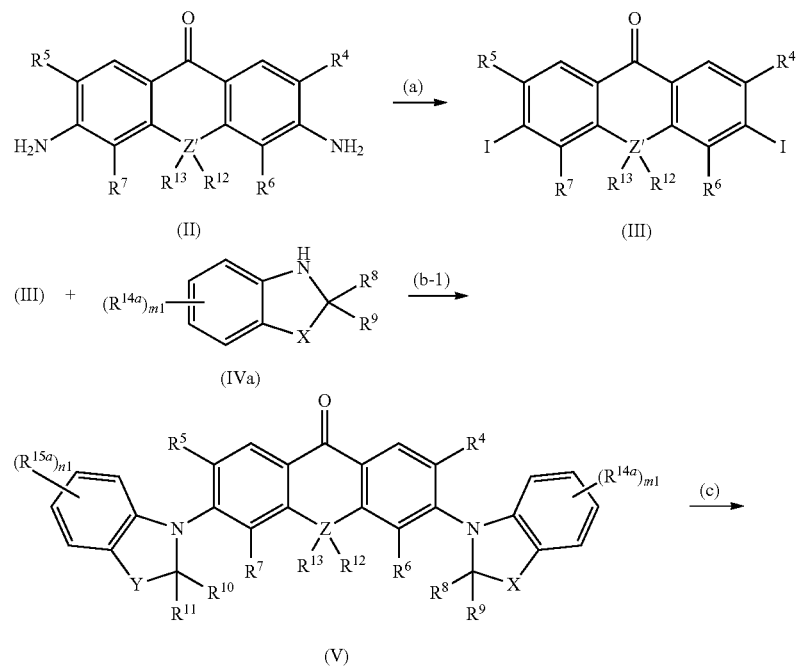

Synthesis scheme 1

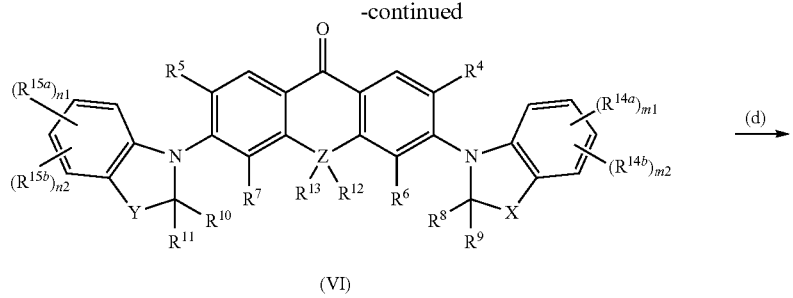

(VI)

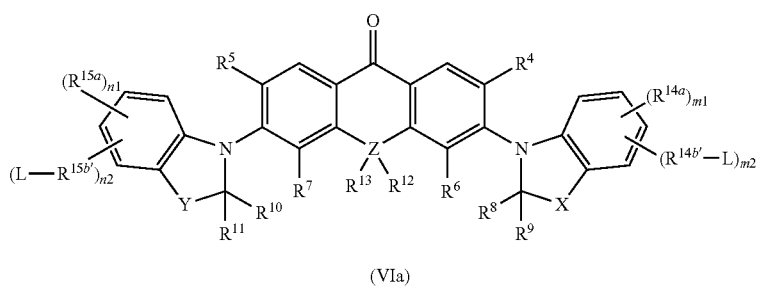

(VIa)

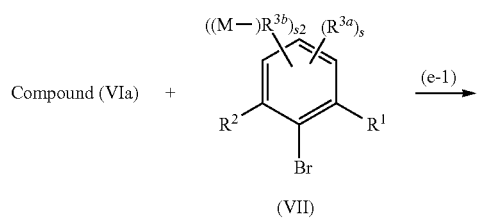

(VII)

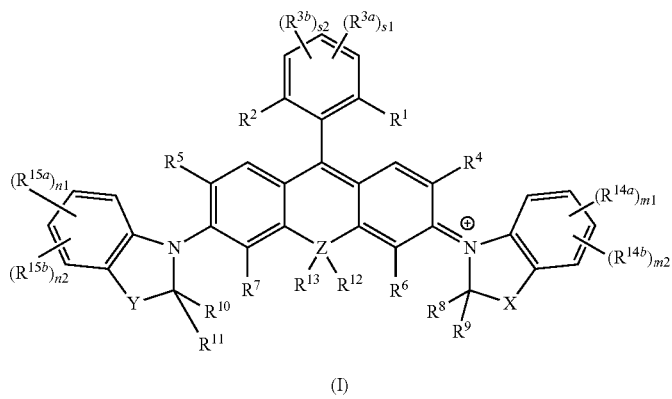

(I)

(1) Step (a)

A compound of general formula (III) (in the formula, $R^4$-$R^7$, $R^{12}$, and $R^{13}$ are as defined in general formula (I)) can be synthesized by dissolving a compound of general formula (II) (in the formula, $R^4$-$R^7$, $R^{12}$, and $R^{13}$ are as defined in general formula (I)) in a mixed solvent of an acidic aqueous solution of hydrochloric acid or the like and an organic solvent, cooling to around 0° C., adding an aqueous solution of 1-2 equivalents of NaNO$_2$ dropwise thereto, stirring for a predetermined time, and adding an aqueous solution of 1-10 equivalents of potassium iodide and reacting.

(2) Step (b-1)

A compound of general formula (V) (in the formula, $R^4$-$R^{13}$, $R^{14a}$, $R^{15a}$, m1, and m2 are as defined in general formula (I)) can be synthesized by dissolving a compound of general formula (III) in an organic solvent such as toluene or the like, adding 1-2 equivalents of a compound of general formula (IVa) (in the formula, $R^8$, $R^9$, $R^{14a}$, and m1 are as defined in general formula (I)) and CsCO$_3$, then adding BINAP and palladium acetate in an argon atmosphere, and reacting for a predetermined time at a temperature of about 100° C.

Furthermore, compounds in which $R^8$ and $R^{10}$, $R^9$ and $R^{11}$, X and Y, $R^{14a}$ and $R^{15a}$, $R^{14a}$ and $R^{15b}$, m1 and n1 in general formula (I) are not the same can also be synthesized by adding a compound of general formula (IVb) (in the formula, $R^{10}$, $R^{11}$, $R^{15a}$, and n1 are as defined in general formula (I)) together with a compound of general formula (VIa) and reacting or by crudely refining an intermediate after the reaction with (IVa) and again reacting with (IVb) under the same conditions.

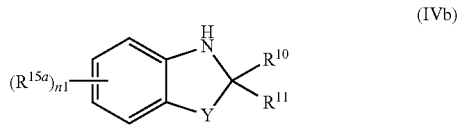

(IVb)

(3) Step (c)

A compound of general formula (VI) (in the formula, $R^4$-$R^{15b}$, m1, m2, n1, and n2 are as defined in general formula (I)) can be synthesized by dissolving a compound of general formula (V) in an organic solvent such as chloroform or the like, cooling to about 0° C. on an ice bath, and then reacting with chlorosulfonic acid.

(4) Step (d)

A compound of formula (VIa) can be synthesized by dissolving a compound of general formula (V) in an alcohol-based solvent such as isopropanol or the like, adding 1-10 equivalents of a reagent for protecting ionic groups such as sulfonic acid groups or the like (for example, triisopropyl orthoformate or the like), and reacting for a predetermined time at 60–80° C.

(5) Step (e-1)

A compound of general formula (I) (where, m2 and n2 are 1 or higher, and $R^{14b}$, $R^{15b}$ are sulfone groups) can be synthesized by dissolving 2-10 equivalents of a compound of general formula (VII) (in the formula, $R^1$-$R^3$, s1, and s2 are as defined in general formula (I), and M, when present, is a protecting group of $R^{3b}$; examples of protecting groups include a t-butyl group and oxazoline group) in an organic solvent such as dehydrated THF or the like, adding a THF solution of 2-10 equivalents of sec-butyl lithium in an argon atmosphere, then adding a THF solution of a compound of general formula (VIa), heat refluxing for a predetermined time, then returning to room temperature and adding hydrochloric acid solution or the like, and heat refluxing again for a predetermined time.

Here, when a protecting group M of $R^{3b}$ is present, the protecting group M is eliminated by adding hydrochloric acid solution or the like and heat refluxing.

Synthesis scheme 2

Step (a) is the same as in the synthesis scheme 1.

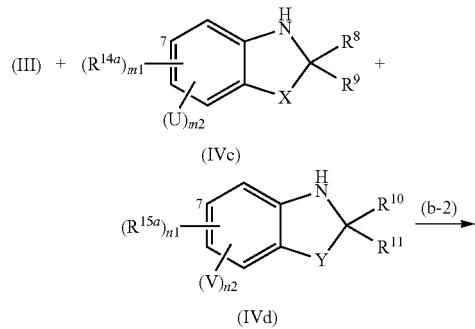

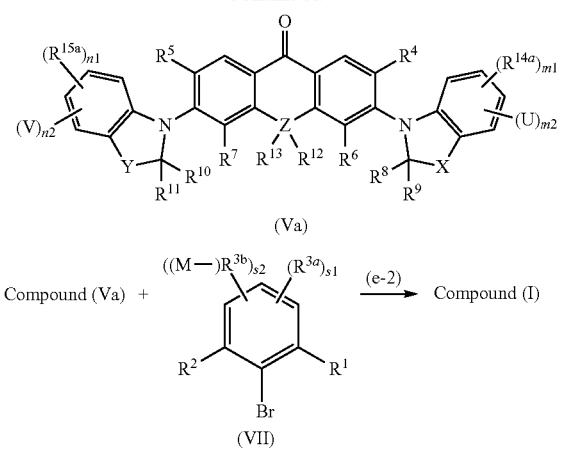

Step (b-2)

A compound of general formula (Va) (in the formula, $R^4$-$R^{13}$, $R^{14a}$, $R^{15a}$, m1, and n1 are as defined in general formula (I), and U and V, respectively, are as defined in general formulas (IVc) and (IVd)) can be synthesized by dissolving a compound of general formula (III) in an organic solvent such as toluene or the like, adding 1-2 equivalents of a compound of general formula (IVc) (in the formula, $R^8$, $R^9$, $R^{14a}$, and m1 are as defined in general formula (I), U represents $R^{14b}$ or a substituent that can be converted into $R^{14b}$), 1-2 equivalents of a compound of general formula (IVd) (in the formula, $R^{10}$, $R^{11}$, $R^{15a}$, and n1 are as defined in general formula (I), and V represents $R^{15b}$ or a substituent that can be converted into $R^{15b}$), and $CsCO_3$, then adding BINAP and palladium acetate in an argon atmosphere, and reacting for a predetermined time at a temperature of about 100° C.

Here, examples of substituents that can be converted into $R^{14b}$ or $R^{15b}$ of U and V include a carbonyl group, halogen group, phosphoric acid ester group, and sulfonic acid ester group.

Step (e-2)

A compound of general formula (I) (where, m2 and n2 are 1 or higher) can be synthesized by dissolving 2-10 equivalents of a compound of general formula (VII) (in the formula, $R^1$-$R^3$, s1, and s2 are as defined in general formula (I), and M, when present, is a protecting group of $R^{3b}$; examples of protecting groups include a t-butyl group and oxazoline group) in an organic solvent such as dehydrated THF, adding 2-10 equivalents of sec-butyl lithium in an argon atmosphere, then adding a THF solution of a compound of general formula (Va) and heat refluxing for a predetermined time, then returning to room temperature and adding a hydrochloric acid solution or the like, and again heat refluxing for a predetermined time.

Here, when a protecting group M of $R^{3b}$ is present, the protecting group M is eliminated in the same way as in the method described in step (e-1).

In addition, when U and V, respectively, are a substituent that can be converted into $R^{14b}$ and a substituent that can be converted into $R^{15b}$, a step of converting U and V, respectively, into $R^{14b}$ and $R^{15b}$ may be included before, during, or after step (e-2). A hydrolysis reaction of an ester protecting group, for example, exists for conversion into $R^{14b}$ and $R^{15b}$.

Synthesis scheme 3

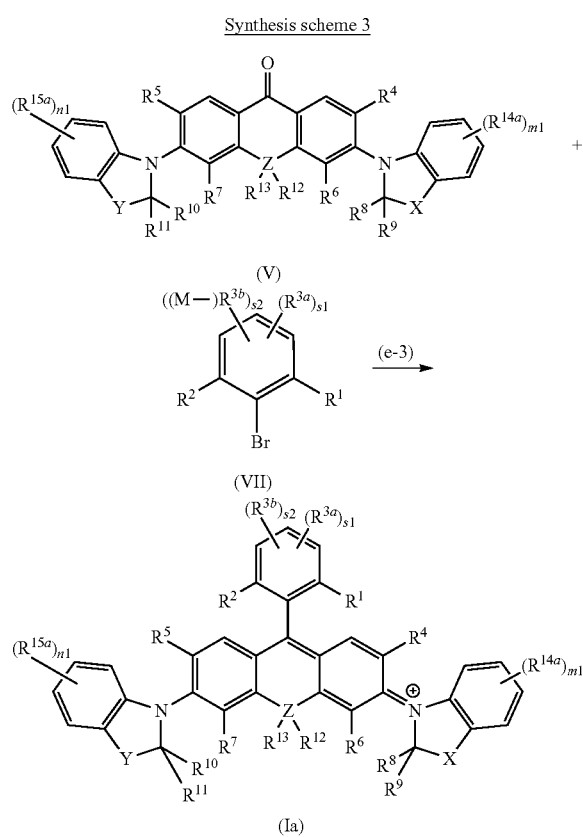

Steps (a) - (b) are the same as in synthesis scheme 1.

Step (e-3)

A compound of general formula (Ia) can be synthesized by dissolving 2-10 equivalents of a compound of general formula (VII) in an organic solvent such as dehydrated THF or the like, adding a THF solution of 2-10 equivalents of sec-butyl lithium in an argon atmosphere, then adding a THF solution of a compound of general formula (V) and heat refluxing for a predetermined time, then returning to room temperature and adding hydrochloric acid solution or the like, and again heat refluxing for a predetermined time.

Here, when a protecting group M of $R^{3b}$ is present, the protecting group M is eliminated in the same way as in the method described in step (e-1).

Compounds represented by general formula (I) or salts thereof are extremely useful as a quencher skeleton. Therefore, compounds of the present invention represented by general formula (I) or salts thereof can be used as a scaffold structure of a fluorescent probe to specifically measure protons, metal ions, active oxygen species, enzymes, or the like (these are sometimes referred to hereinafter as "objects of measurement") by being bonded with a fluorescent dye, preferably via a linker. Compounds of the present invention represented by general formula (I) or salts thereof can also be used as a scaffold structure of a fluorescent labeling reagent for fluorescent labeling of biological components by being bonded with a fluorescent dye, preferably via a linker. Such fluorescent probes make it possible to detect various enzymatic reactions and the like by cleavage of the bonds between the fluorescent dye and quencher by an enzymatic reaction or the like, formation of an active fluorescent dye, and measurement of the fluorescence of this fluorescent dye.

For example, it is possible to utilize a residue of a compound represented by general formula (I) in the production of a fluorescent probe capable of detecting protons, metal ions, active oxygen species, enzymes, or the like. A residue of a compound of general formula (I) can also be utilized in the production of a fluorescent labeling reagent for fluorescent labeling of biological components.

Therefore, one embodiment of the present invention is a fluorescent probe capable of detecting protons, metal ions, active oxygen species, enzymes, or low-oxygen environments, or the like wherein the fluorescent probe comprises a residue of a compound represented by general formula (I).

Another embodiment of the present invention is a fluorescent labeling reagent wherein the fluorescent labeling reagent comprises a residue of a compound represented by general formula (I).

The term "residue" in this specification means a chemical structure remaining after removing one or more hydrogen atoms from a compound represented by general formula (I).

Another aspect of the present invention is a fluorescent probe comprising a compound having a structure in which a residue of a compound represented by general formula (I) is bonded with a fluorescent dye, via a linker when present.

In addition, another aspect of the present invention is a fluorescent labeling reagent comprising a compound having a structure in which a residue of a compound represented by general formula (I) is bonded with a fluorescent dye, via a linker when present.

In the present invention, conventional, known near-infrared fluorescent dyes can be used as a fluorescent dye. Examples of such near-infrared fluorescent dyes include Cy7 (GE Healthcare), Cy7.5, ICG, Dy730, DY750, DY780 (Dyomics GmbH), Alexa fluor 680, Alexa fluor 700, Alexa fluor 750, Alexa fluor 790 (life technology), and the like.

A linker is selected so that the compound represented by general formula (I) can act as a quencher on the near-infrared fluorescent dye. However, as long as it has this property, the type of linker is not particularly restricted. A linker may be a linker comprising only a carbon atom, or it may be a linker containing one or more hetero atoms such as a nitrogen atom, sulfur atom, oxygen atom, or the like. A linker may be linear, branched, cyclic, or a combination of these. For example, the number of linking atoms in the linker is from about 1 to 9, preferably from about 1 to 6. In this specification, the number of linking atoms in the linker means the number of atoms contained in the shortest path from the atom at one end of the linker to the atom at the other end. The linker may have one or more substituents.

When a compound of general formula (I) bonds with a near-infrared fluorescent dye via a linker, at least one $R^{3b}$ is preferably a substituent selected from a hydroxyl group, carboxy group, sulfonyl group, alkoxycarbonyl group, or amino group. The bonding mode of the compound of general formula (I) and the linker at this time is not particularly restricted; examples include amide bonding, ester bonding, sulfoamide bonding, and the like.

A fluorescent group can be introduced easily into the compound of the present invention if at least one $R^{3b}$ is such a substituent.

Examples of linkers include alkyl linkers, polyethylene glycol linkers, peptide linkers, DNA linkers, RNA linkers, and other such linkers.

Examples of the object of measurement of a fluorescent probe of the present invention include, as metal ions, sodium ions, lithium ions, and other such alkali metal ions, calcium ions and other such alkaline earth metal ions, magnesium ions, zinc ions, and the like. As active oxygen species, examples include nitric oxide, hydroxyl radicals, singlet oxygen, superoxides, peroxynitrites, hypochlorous acid, and the like. As enzymes, examples include cathepsin, elastase, MMP, and the like. Biological components such as GSH, cysteine, and the like can also be given as examples of objects of measurement of a fluorescent labeling reagent of the present invention. Moreover, objects of measurement are not limited to these.

The method of using a fluorescent probe of the present invention is not particularly restricted; examples include measurement of the activity of isolated, purified enzymes and enzymes to be measured contained in cell lysate, measurement of enzymatic activity in live cells, measurement of the activity of enzymes that serve as cancer biomarkers in living tissues by taking advantage of the optical characteristic of long wavelength, and the like.

A fluorescent probe comprising a compound represented by general formula (I) of the present invention can also be used suitably in the measurement of active oxygen species, for example, $H_2O_2$, —OCl, $ONOO^-$, $O_2^-$, and hydroxyl radicals.

EXAMPLES

The present invention is explained more concretely below through examples, but the scope of the present invention is not limited to the following examples.

Comparative Example 1

A comparative compound 1 was synthesized according to synthesis scheme 3 below.

(1) Synthesis of I—Si-Xanthone

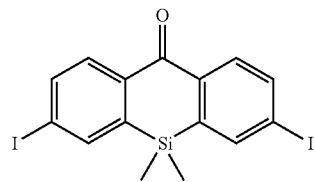 [SMILES: C[Si]1(C)c2cc(I)ccc2C(=O)c2ccc(I)cc21]

$NH_2$—Si-xanthone (228 mg, 0.85 mmol) was dissolved in 4 mL of a 2N HCl aqueous solution and 4 mL of acetonitrile, and cooled to 0° C. on an ice bath. $NaNO_2$ (140 mg, 1.70 mmol) dissolved in 1 mL of water was added dropwise thereto under stirring. After stirring for 30 minutes, KI (2.82 g, 8.50 mmol) dissolved in 2 mL of water was added dropwise under stirring vigorously. After stirring for one hour, saturated sodium sulfite aqueous solution was added, the compound was extracted using $CH_2Cl_2$, the solvent of the organic layer was removed, purification was performed by column chromatography (silica gel, $CH_2Cl_2$), and I—Si-xanthone (72 mg, yield 17%) was obtained.

$^1$H NMR (300 MHz, CDCl3): δ 0.51 (s, 6H), 7.92 (dd, J=8.10 Hz, J=1.50 Hz, 2H), 7.98 (d, J=1.5 Hz, 2H), 8.09 (d, J=8.10 Hz, 2H). $^{13}$C NMR (300 MHz, DMSO): δ −1.65, 101.8, 131.8, 131.4, 139.5, 139.5, 140.9, 141.8, 187.0.

Synthesis scheme 4

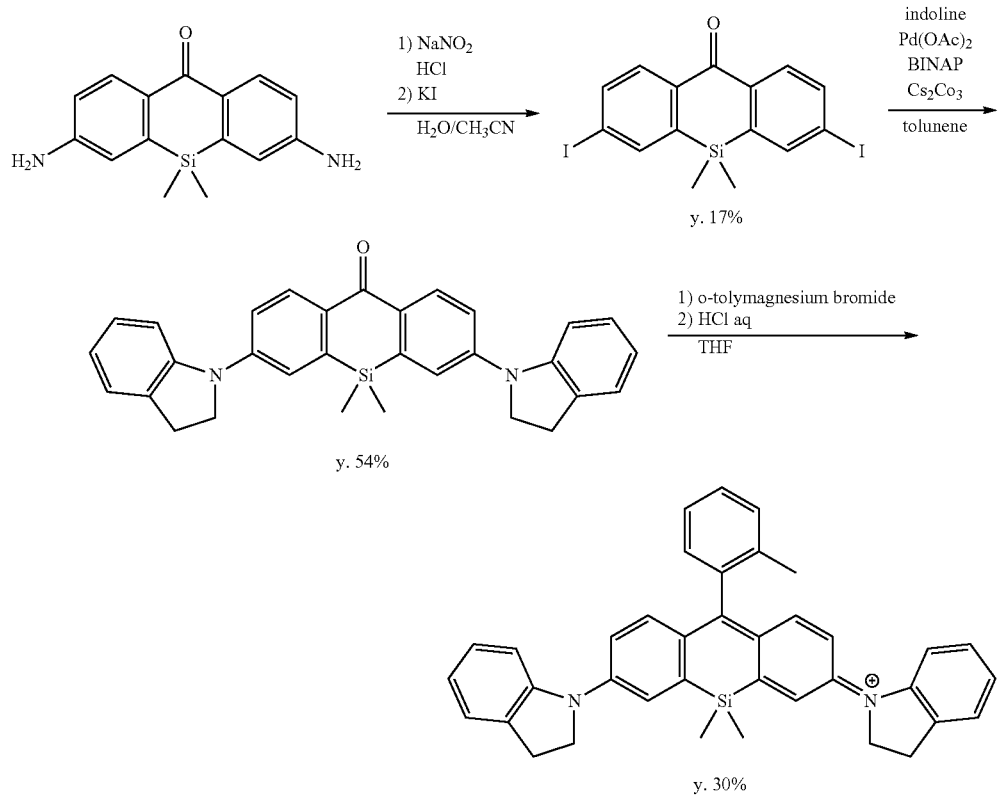

Comparative compound 1

(2) Synthesis of Indoline-Si-Xanthone

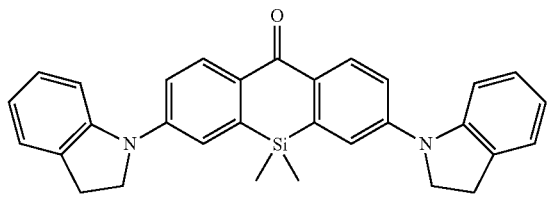 [SMILES: C[Si]1(C)c2cc(N3CCc4ccccc43)ccc2C(=O)c2ccc(N3CCc4ccccc43)cc21]

I—Si-xanthone (60 mg, 0.12 mmol) was placed in a 50 mL Schlenk tube, and dissolved in 10 mL of toluene. Indoline (28 mg, 0.24 mmol) and $Cs_2CO_3$ (78 mg, 0.24 mmol) were added thereto, followed by degassing and argon exchanging. BINAP (7.4 mg, 0.01 mmol) and Pd(OAC)$_2$ (2.6 mg, 0.01 mmol) were added in an argon atmosphere, and stirred overnight at 100° C. After filtration, the solvent was removed, purification was performed by column chromatography (silica gel, $CH_2Cl_2$/hexane=8/2), and indoline-Si-xanthone (31 mg, yield 54%) was obtained.

$^1$H NMR (300 MHz, CDCl$_3$): δ 0.52 (s, 6H), 3.20 (t, J=8.10 Hz, 4H), 4.10 (t, J=8.10 Hz, 4H), 6.86 (t, J=7.50 Hz, 2H), 7.16 (t, J=7.50 Hz, 2H), 7.23 (d, J=7.20 Hz, 2H), 7.31-7.37 (m, 4H), 7.42 (d, J=3.0 Hz, 2H), 8.47 (d J=9.00 HZ, 2H); $^{13}$C NMR (300 MHz, DMSO): δ −1.20, 28.1, 51.8, 109.6, 117.6, 119.1, 120.3, 125.4, 127.2, 131.5, 132.1, 133.0, 140.4, 145.4, 146.3; HRMS(ESI+): Calcd for [M+H]+, 473.2049. found, 473.2007 (−4.2 mmu).

(3) Synthesis of 2-Me-Si-QSY21 (Comparative Compound 1)

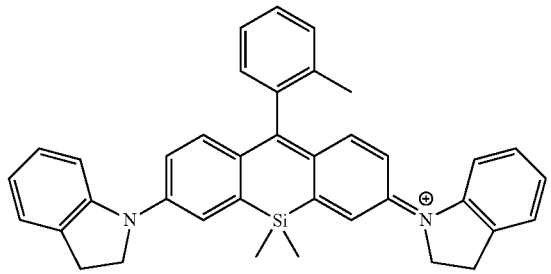 [SMILES: Cc1ccccc1C1=C2C=C/C(=[N+]3/CCc4ccccc43)C=C2[Si](C)(C)c2cc(N3CCc4ccccc43)ccc21]

Indoline-Si-xanthone (44 mg, 0.09 mmol) was dissolved in 5 mL of dehydrated THF, argon exchanging was performed, and heat refluxed at 80° C. One milliliter (1 mmol) of a THF solution of 1 M o-tolylmagnesium bromide was added thereto, and heat refluxed for three hours at 80° C. The solution was subsequently returned to room temperature, 2N HCl solution was added, and stirred for 15 minutes. After elution by $CH_2Cl_2$, the solvent was removed, purification was performed by HPLC, and 2-Me-Si-QSY21 (15 mg, yield 30%) was obtained.

$^1$H NMR (300 MHz, CD$_3$CN): δ 0.65 (s, 6H), 2.16 (s, 3H), 3.26 (t, J=8.10 Hz, 4H), 4.32 (t, J=8.10 Hz, 4H), 7.12-7.49 (m, 16H), 7.57 (d, J=8.10 Hz, 2H), 7.72 (d, J=2.40 Hz, 2H); $^{13}$C NMR (300 MHz, CDCl$_3$): δ −1.5, −1.1, 19.5, 28.2. 53.1, 114.5, 117.2, 124.0, 125.6, 126.4, 127.8, 128.9, 129.2, 130.4, 130.5, 135.5, 135.7, 138.1, 141.7, 142.0, 148.8, 149.5; HRMS (ESI+): Calcd for [M]+, 547.2570. found, 547.2536 (−3.4 mmu).

(4) Absorption-Fluorescence Profile of 2-Me-Si-QSY21

The absorption spectra and fluorescence spectra (excitation wavelength 760 nm) of 1 M PBS, methanol, DMF, and chloroform solutions of comparative compound 1 (each containing 0.1% DMSO as cosolvent) were measured. The results are shown in FIG. 1. Table 1 shows the photophysical properties of the comparative compound 1 obtained.

TABLE 1

| Photophysical properties of 2-Me—Si-SQY21 | | |
|---|---|---|
| | $\lambda_{abs.\ max}$ (nm) | $\Phi_{fl}$* |
| PBS | 764 | n.d. |
| MeOH | 779 | n.d. |
| DMF | 790 | n.d. |
| Chloroform | 790 | n.d. |

*For determination of the quantum efficiency of the fluorescence ($\phi_{fl}$), ICG in DMSO ($\phi_{fl}$ = 0.13) was used as a fluorescence standard.

The absorption spectrum of 2-Me-Si-QSY21 reached up to 850 nm, and it had an absorption spectrum in a wavelength region appropriate for a near-infrared light region quencher. The fluorescence quantum yield in both water and organic solvents was low, 0.001 or less.

Comparative Example 2

A compound having a sulfone group introduced into comparative compound 1 (comparative compound 2) was synthesized according to the synthesis scheme below.

Synthesis scheme 5

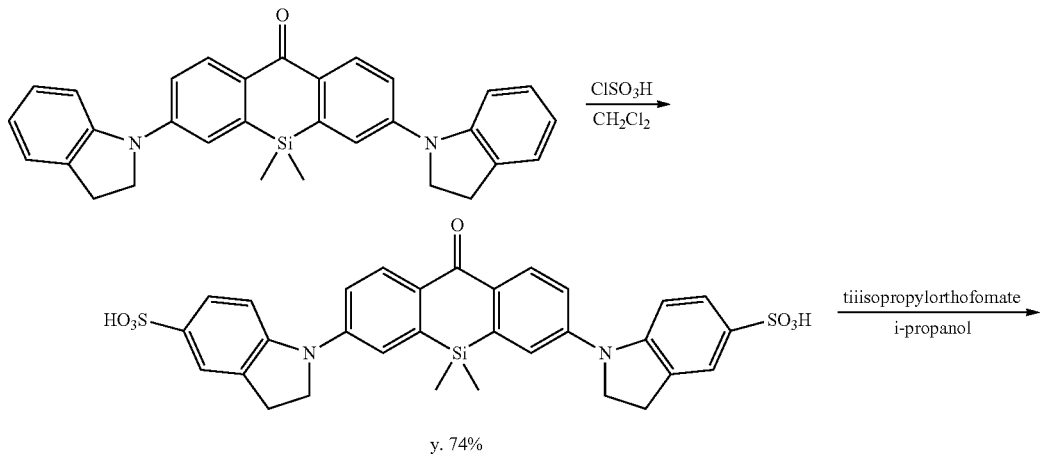

y. 74%

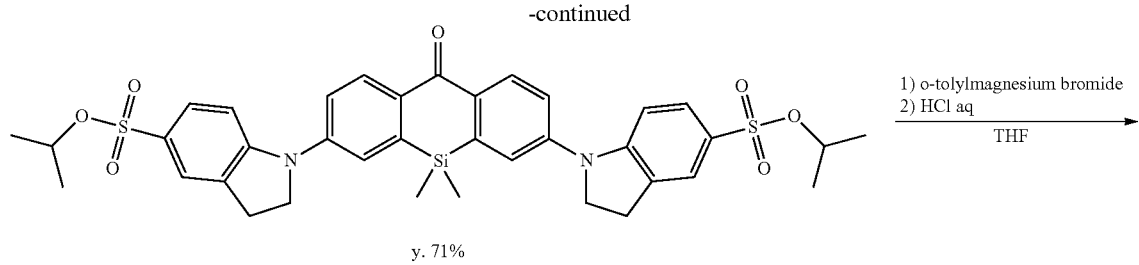

y. 71%

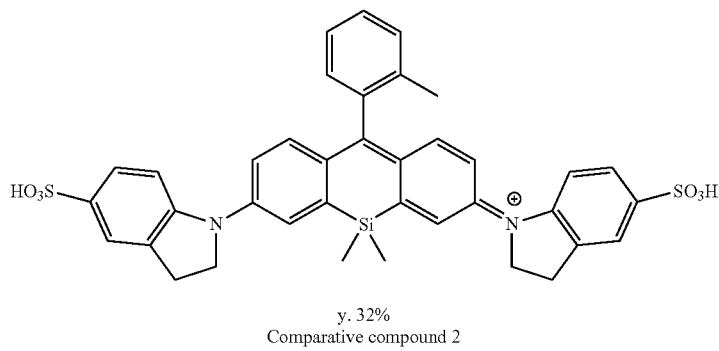

y. 32%
Comparative compound 2

(1) Synthesis of SO₃H-Indoline-Si-Xanthone

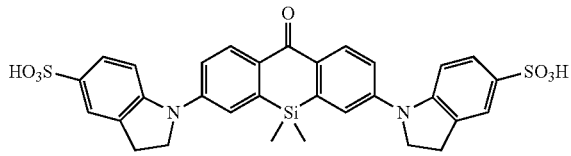 [SMILES: C[Si]1(C)c2cc(N3CCc4cc(S(=O)(=O)O)ccc43)ccc2C(=O)c2ccc(N3CCc4cc(S(=O)(=O)O)ccc43)cc21]

Indoline-Si-xanthone (400 mg, 0.93 mmol) was dissolved in 10 mL of CH₂Cl₂, and cooled to 0° C. on an ice bath. CASO₃H (259 mg, 204 μL, 2.23 mmol) was added dropwise thereto under stirring. After confirming the progress of the reaction by TLC, water was added, the organic solvent alone was distilled off under reduced pressure, the aqueous layer was purified by HPLC, and SO₃H-indoline-Si-xanthone (465 mg, yield 74%) was obtained.

¹H NMR (300 MHz, DMSO): δ 0.54 (s, 6H), 3.22 (t, J=9.00 Hz, 4H), 4.15 (t, J=9.00 Hz, 4H), 7.29 (d, J=8.70 Hz, 2H), 7.45 (dd, J=2.40, 8.70 Hz, 2H), 7.49 (s, 2H), 7.63-7.66 (m, 4H), 8.37 (d, 8.70 Hz, 2H); ¹³C NMR (75 MHz, CDCl₃): δ −1.44, 27.1, 51.7, 108.1, 117.5, 119.5, 122.9, 125.1, 130.8, 131.8, 132.1, 140.1, 140.5, 144.9, 145.7, 183.6; HRMS (ESI-): Calcd for [M−H]−, 630.0951. found, 630.0991 (+4.0 mmu).

(2) Synthesis of SO₃iPr-Indoline-Si-Xanthone

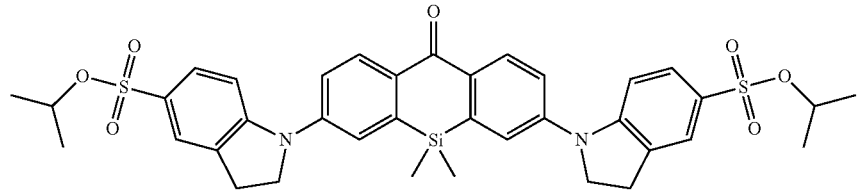 [SMILES: CC(C)OS(=O)(=O)c1ccc2c(c1)CCN2c1ccc2c(c1)[Si](C)(C)c1cc(N3CCc4cc(S(=O)(=O)OC(C)C)ccc43)ccc1C2=O]

SO₃H-indoline-Si-xanthone (100 mg, 0.16 mmol) was dissolved in 100 mL of i-propanol, and stirring was conducted for four hours at 55° C. after adding 2 mL of triisopropyl orthoformate. After the target compound had precipitated, it was filtered out and washed with hexane to obtain SO₃iPr-indoline-Si-xanthone (80 mg, yield 71%).

¹H NMR (300 MHz, CDCl₃): δ 0.54 (s, 6H), 1.31 (d, J=6.00 Hz, 12H), 3.27 (t, J=8.70 Hz, 4H), 4.22 (t, J=8.70 Hz, 4H), 4.76 (sep, J=6.00 Hz, 1H), 7.25 (dd, J=1.50, 8.10 Hz, 2H), 7.41-7.46 (m, 4H), 7.69 (s, 2H), 7.70 (dd, J=2.40, 7.80 Hz, 2H), 8.50 (d, J=8.10 Hz, 2H); ¹³C NMR (75 MHz, CDCl3): δ −1.30, 22.9, 27.4, 52.4, 108.0, 119.2, 130.8, 124.6, 127.4, 128.8, 131.7, 132.7, 134.8, 140.5, 145.1, 150.1, 184.9; HRMS (ESI+): Calcd for [M+H]+, 717.2124. found, 717.2169 (+4.5 mmu).

(3) Synthesis of 2-Me-SO₃H—Si-QSY21 (Comparative Compound 2)

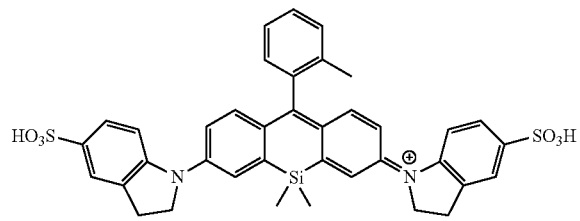 [SMILES: Cc1ccccc1C1=C2C=C/C(=[N+]3/CCc4cc(S(=O)(=O)O)ccc43)C=C2[Si](C)(C)c2cc(N3CCc4cc(S(=O)(=O)O)ccc43)ccc21]

SO₃iPr-indoline-Si-xanthone (13 mg, 0.02 mmol) was dissolved in 5 mL of dehydrated THF, argon exchanging was performed, and heat reflux was performed at 80° C. One milliliter (1 mmol) of a THF solution of 1 M o-tolylmagnesium bromide was added thereto, and heat refluxed for three hours at 80° C. The solution was subsequently returned to room temperature, added with 2N HCl solution, and heat refluxed for three hours at 80° C. After the reaction solution returned to room temperature, purification was performed by HPLC, and 2-Me-SO₃H—Si-QSY21 (4 mg, yield 32%) was obtained.

¹H NMR (300 MHz, DMSO): δ 0.67 (s, 3H), 0.70 (s, 3H), 2.05 (s, 3H), 3.25 (t, J=7.50 Hz, 4H), 4.41 (t, J=7.50 Hz, 4H), 7.15 (d, J=9.10 Hz, 2H), 7.27 (d, J=7.50 Hz, 1H), 7.45-7.59 (m, 11H), 7.82 (d, J=2.10 Hz, 2H); HRMS (ESI-): Calcd for [M-2H]-, 705.1549. found, 705.1586 (+3.7 mmu).

(4) Absorption-Fluorescence Profile of 2-Me-SO₃H—Si-QSY21 in Water

Figure 2:
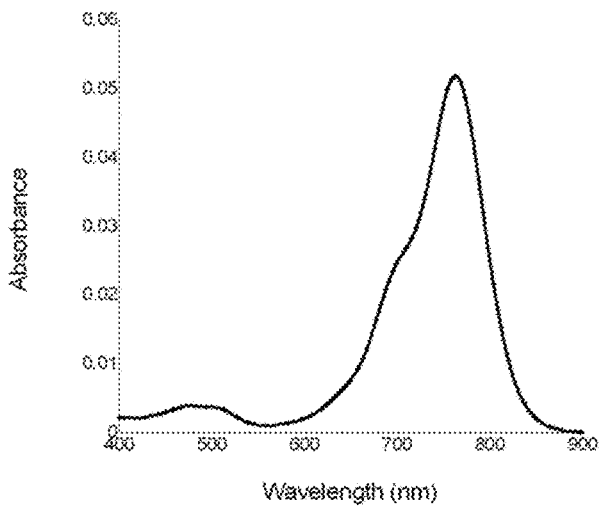
FIG. 2 Absorption spectrum of 2-Me-SO$_3$H—Si-QSY21 (comparative compound 2)

The absorption spectrum of a 1 M PBS solution of comparative compound 2 (containing 0.1% DMSO as cosolvent) was measured. The results are shown in FIG. 2. As can be seen from FIG. 2, no change in absorption wavelength is seen due to introduction of a sulfone group, and the compound has an adequate absorption wavelength as a quencher of the near-infrared light region.

Figure 3:
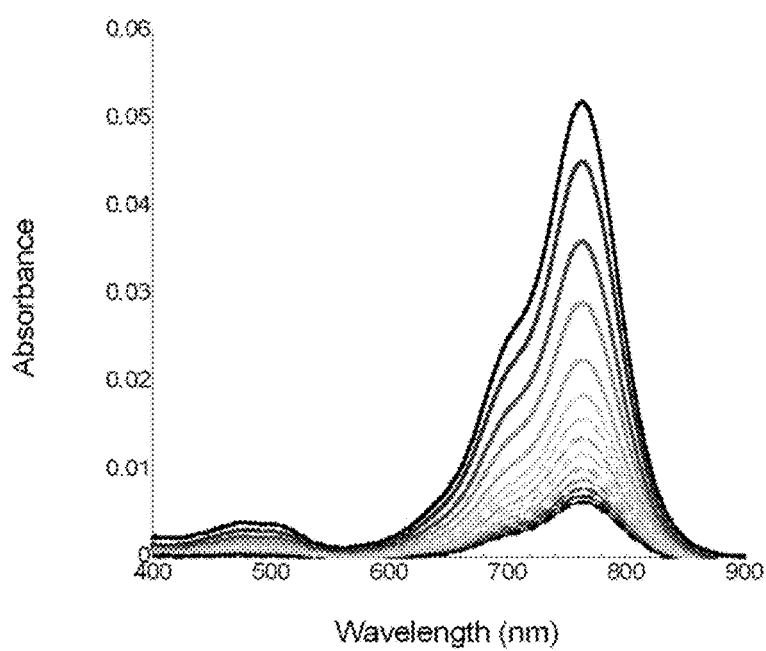
FIG. 3 Changes over time in the absorption spectrum of 2-Me-SO$_3$H—Si-QSY21 (comparative compound 2)

However, when changes over time in the absorption spectrum of comparative compound 2 were examined, a gradual decrease in absorption was observed in water, suggesting instability in water, as shown in FIG. 3. Here, since no increase in new absorption associated with the decrease in the absorption of the quencher was observed at wavelengths of 400 nm or higher, a nucleophilic addition reaction of water molecules was thought to have occurred at position 9 of the xanthene ring.

Examples 1 and 2

Compounds 1 and 2 of the present invention were synthesized in accordance with the following synthesis scheme from SO₃iPR-indoline-Si-xanthone.

(1) Synthesis of 2,6-diMe-SO₃H Indoline-Si-QSY21 (Compound 1)

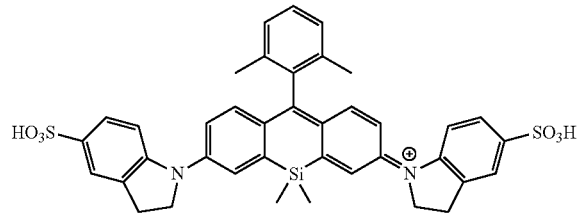 [SMILES: Cc1cccc(C)c1C1=C2C=C/C(=[N+]3/CCc4cc(S(=O)(=O)O)ccc43)C=C2[Si](C)(C)c2cc(N3CCc4cc(S(=O)(=O)O)ccc43)ccc21]

2-Bromo-m-xylene (28 mg, 0.15 mmol) was dissolved in 5 mL of dehydrated THF under argon purge, and cooled to -78° C. Thereafter, 150 µL of 1 M sec-BuLi THF solution was added under stirring. After stirring for 30 minutes, SO₃iPR-indoline-Si-xanthone (11 mg, 0.015 mmol) was dissolved in 5 mL of dehydrated THF, and added. After addition, the solution was returned to room temperature, heated to 60° C., and stirred for two hours. After stirring, 2N HCl solution was added, and heat reflux was carried out for two hours. After distilling off the organic solvent under reduced pressure, purification was performed by HPLC, and 2,6-diMe-SO₃H indoline-Si-QSY21 (5 mg, yield 46%) was obtained.

¹H NMR (300 MHz, DMSO): δ 0.70 (s, 6H), 2.05 (s, 6H), 3.33 (br, 4H), 4.43 (t, 6.60 Hz, 4H), 7.27-7.43 (m, 7H), 7.62 (d, J=8.70 Hz, 2H), 7.75-7.84 (m, 6H); HRMS (ESI-): Calcd for [M-2H]-, 719. 1706. found, 709. 1702 (-0.4 mmu).

(2) Synthesis of 2,6-diOMe-SO₃H Indoline-Si-QSY21 (Compound 2)

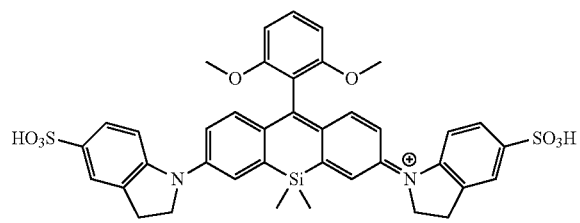 [SMILES: COc1cccc(OC)c1C1=C2C=C/C(=[N+]3/CCc4cc(S(=O)(=O)O)ccc43)C=C2[Si](C)(C)c2cc(N3CCc4cc(S(=O)(=O)O)ccc43)ccc21]

Synthesis scheme 6

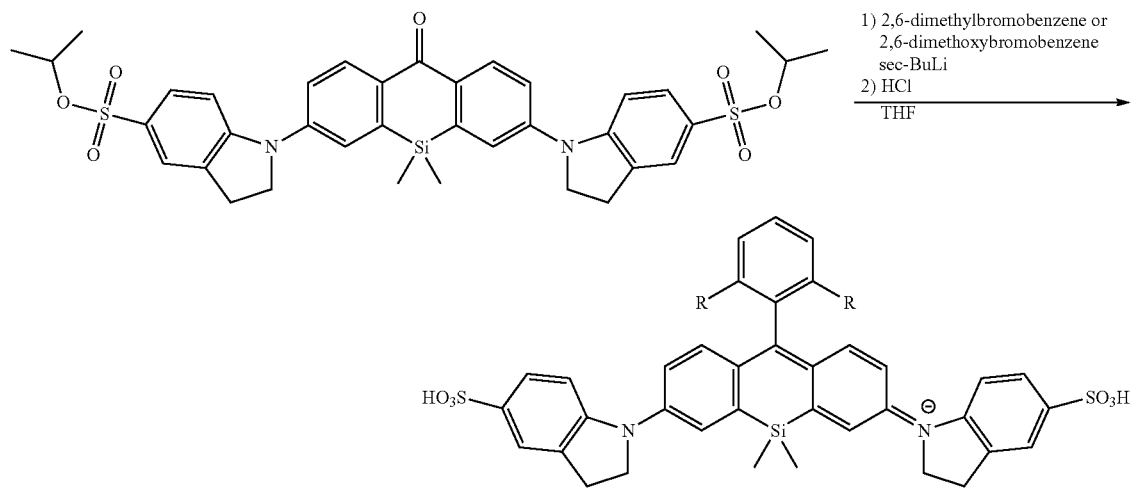

Compound 1 (R: methyl group)
Compound 2 (R: methoxy group)

2,6-Dimethoxybromobenzene (32.6 mg, 0.15 mmol) was dissolved in dehydrated THF under argon purge, and cooled to −78° C. Thereafter, 150 μL of 1 M sec-BuLi THF solution was added under stirring. After stirring for 30 minutes, SO₃iPr-indoline-Si-xanthone (14 mg, 0.02 mmol) was dissolved in 5 mL of dehydrated THF, and added. After addition, the solution was returned to room temperature, heated to 60° C., and stirred for two hours. After stirring, 2N HCl solution was added, and heat reflux was carried out for two hours. After distilling off the organic solvent under reduced pressure, purification was performed by HPLC, and 2,6-diOMe-SO₃H indoline-Si-QSY21 (6 mg, yield 41%) was obtained.

¹H NMR (300 MHz, DMSO): δ 0.66 (s, 6H), 3.24 (t, J=7.50 Hz, 4H), 3.66 (s, 6H), 4.39 (t, J=7.50 Hz, 4H), 6.93 (d, J=8.70 Hz, 2H), 7.30 (d, J=9.60 Hz, 2H), 7.43 (dd, J=2.10, 9.60 Hz, 2H), 7.49-7.61 (m, 7H), 7.78 (d, J=2.10 Hz, 2H); HRMS (ESI−): Calcd for [M−2H]−, 751.1604. found, 751.1567 (−3.7 mmu).

(3) Absorption Profiles of Compounds 1 and 2

Figure 4A:
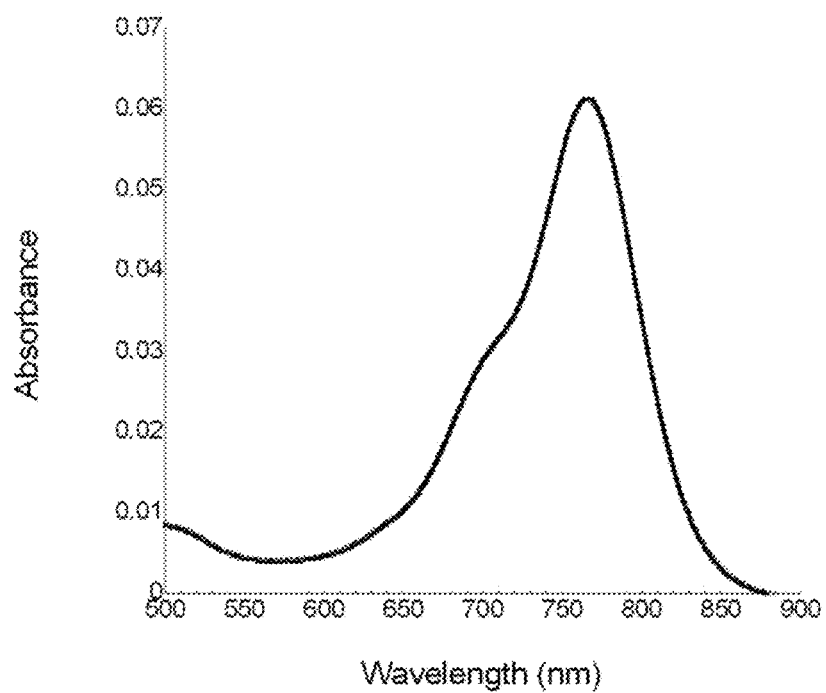
FIG. 4a Changes over time in the absorption spectrum of compound 1 of the present invention FIG. 4b Changes over time in the absorption spectrum of compound 2 of the present invention FIG. 5 Absorption spectrum of compound 1 (right) and compound 4 (left) in PBS (1% DMSO)
Figure 4B:
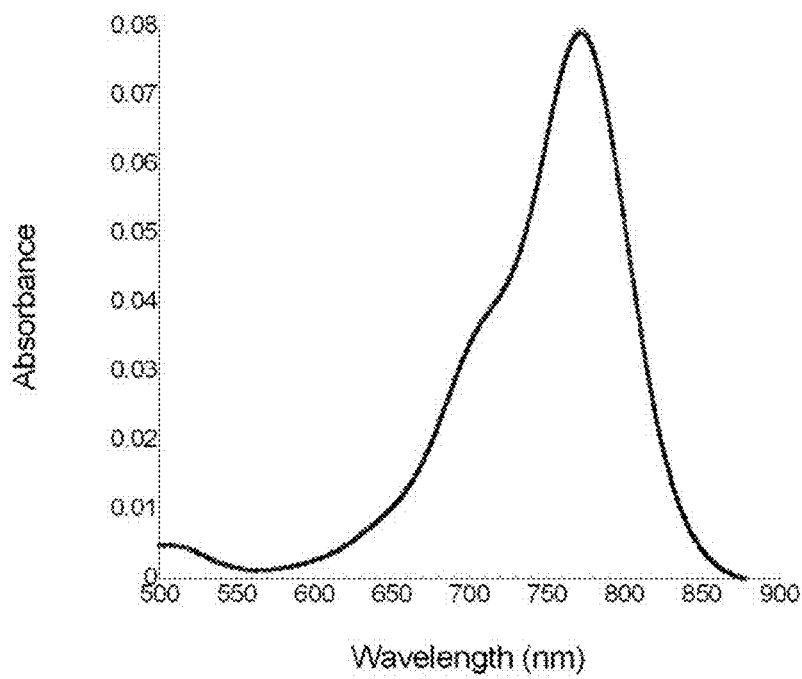

The changes over time in the absorption spectra of PBS solutions of compounds 1 and 2 (containing 0.1% DMSO as cosolvent) were measured. The results are shown in FIG. 4a and FIG. 4b.

As shown in FIG. 4, no decrease in absorption in water was observed for both compounds 1 and 2. It is thought based on this result that the introduction of substituents at the ortho positions of the benzene ring bonded to position 9 of the xanthene ring suppresses nucleophilic attack to position 9 of the xanthene ring and improves the stability of the compound in water.

Example 3

Compound 3 was synthesized from SO₃H-indoline-Si-xanthone in accordance with the following synthesis scheme.

a) 2-(4-Bromo-3,5-dimethoxyphenyl)-4,4-dimethyl-4,5-dihydrooxazole, sec-BuLi, THF, 60° C., ii) 2N HCl aq, acetone, reflux, 2 days, y. 60%

Synthesis of 2,6-diOMe-SO₃H Indoline-Si-QSY21 COOH (Compound 3)

2-(4-Bromo-3,5-dimethoxyphenyl)-4,4-dimethyl-4,5-dihydrooxazole (65 mg, 0.21 mmol) was dissolved in 5 mL of dehydrated THF under argon purge, and cooled to −78° C. Thereafter, 210 μL of 1 M sec-BuLi THF solution was added under stirring. After stirring for 30 minutes, SO₃iPr-indoline-Si-xanthone (30 mg, 0.042 mmol) was dissolved in 5 mL of dehydrated THF, and added. After addition, the solution was returned to room temperature, heated to 60° C., and stirred for two hours. After stirring, 6N HCl solution was added, and heat reflux was carried out for two hours. After distilling off the organic solvent under reduced pressure, purification was performed by HPLC, and compound 3 (2,6-diOMe-SO₃H indoline-Si-QSY21 COOH) (20 mg, 0.025 mmol, yield 60%) was obtained.

Example 4

Compound 4 of the present invention was synthesized in accordance with the following synthesis scheme.

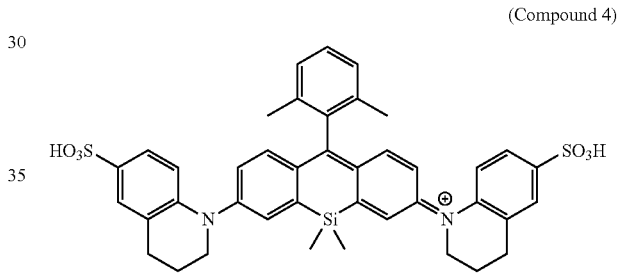

(Compound 4)

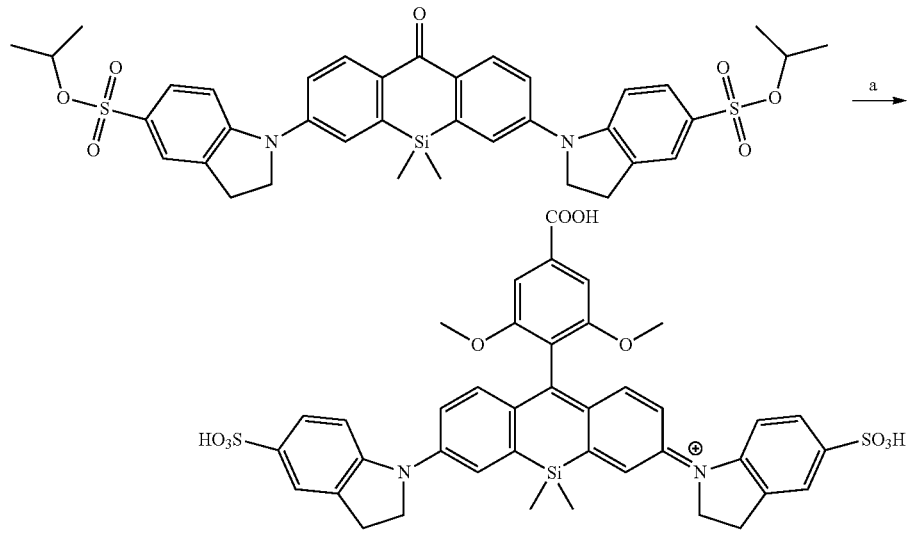

Synthesis scheme 7

Compound 3

Synthesis scheme 8

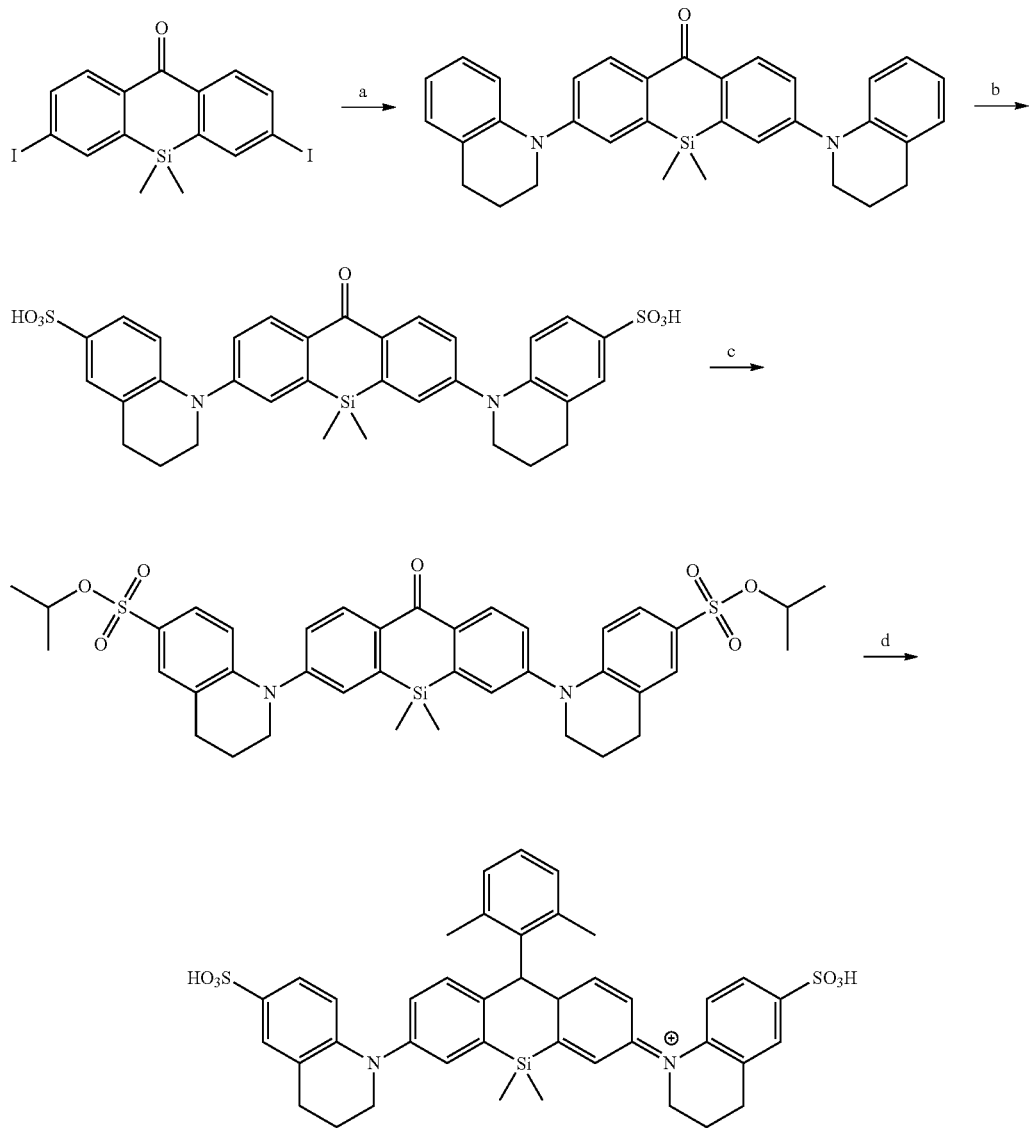

a) 1,2,3,4-tetrahydroqunoline, Pd(OAc)$_2$, BINAP, Cs$_2$CO$_3$, toluene, 80° C., 60%; b) ClSO$_3$H, CH$_2$Cl$_2$, quant; c) i) oxalyl chloride, DMF, CH$_2$Cl$_2$, ii) isopropanol, pyridine, 35%; d) i) 2-bromo-m-xylene, sec-BuLi, THF, −78° C., ii) 2N HCl aq., reflux, 54%.

(1) Synthesis of Tetrahydroquinoline-Si-Xanthone

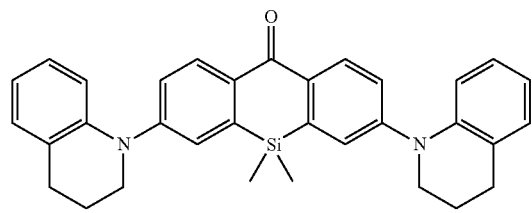 [SMILES: C[Si]1(C)c2cc(N3CCCc4ccccc43)ccc2C(=O)c2ccc(N3CCCc4ccccc43)cc21]

I—Si-xanthone (245 mg, 0.50 mmol) was placed in a 50 mL Schlenk tube, and dissolved in 10-20 mL of toluene. Tetrahydroquinoline (1.33 g, 2.00 mmol) and Cs$_2$CO$_3$ (3.25 g, 2.00 mmol) were added thereto, followed by degassing and argon exchanging. BINAP (62 mg, 0.05 mmol) and Pd(OAc)$_2$ (22 mg, 0.05 mmol) were added in an argon atmosphere, and stirred overnight at 100° C. After the solution had returned to room temperature, water was added, and the solution was extracted by CH$_2$Cl$_2$. The organic layer was dehydrated by sodium sulfate, and the solvent was removed. The product was then purified by column chromatography (silica gel, CH$_2$Cl$_3$/hexane=1/1), and tetrahydroquinoline-Si-xanthone (150 mg, yield 60%) was obtained.

$^1$H NMR (300 MHz, CDCl$_3$): δ 0.43 (s, 6H), 2.06 (qt, J=6.0 Hz, 4H), 2.82 (t, J=6.0 Hz, 4H), 3.74 (t, J=6.0 Hz, 4H), 6.87 (t, J=7.5 Hz, 2H), 7.04 (dt, J=1.5, 8.7 Hz, 2H), 7.12 (d, J=7.5 Hz, 2H), 7.28 (d, J=8.1 Hz, 2H), 7.34 (dd, J=3.0, 9.0 Hz, 2H), 7.41 (d, J=2.4 Hz, 2H), 8.39 (d, J=8.7 Hz, 2H); $^{13}$C NMR (75 MHz, CDCl$_3$): δ −1.43, 23.6, 27.4, 49.1, 118.7, 120.9, 121.8, 123.6, 126.3, 128.4, 129.3, 131.3, 134.1, 140.2, 142.1, 150.4, 185.3; HRMS (ESI+): Calcd for [M+H]+, 501.2362. found, 501.2412 (+5.0 mmu).

(2) Synthesis of SO₃H-Tetrahydroquinoline-Si-Xanthone

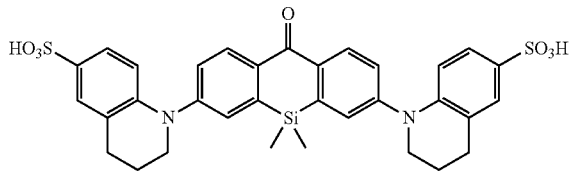 [SMILES: C[Si]1(C)c2cc(N3CCCc4cc(S(=O)(=O)O)ccc43)ccc2C(=O)c2ccc(N3CCCc4cc(S(=O)(=O)O)ccc43)cc21]

Tetrahydroquinoline-Si-xanthone (50 mg, 0.10 mmol) was dissolved in 10 mL of CH₂Cl₂, and cooled to 0° C. on an ice bath. ClSO₃H (182 μL) was added dropwise thereto, and the solution was stirred for two hours at 0° C. Thereafter, after stopping the reaction by adding water, the CH₂Cl₂ was removed by distillation under reduced pressure, the remaining aqueous solution was purified by HPLC, and SO₃H-tetrahydroquinoline-Si-xanthone (78 mg, quant) was obtained.

¹H NMR (300 MHz, DMSO): δ 0.46 (s, 6H), 1.97 (q, J=6.0 Hz, 4H), 2.76 (t, J=6.0 Hz, 4H), 3.74 (t, J=6.0 Hz, 4H), 7.03 (d, J=8.1 Hz, 2H), 7.27 (d, J=8.1 Hz, 2H), 7.38-7.42 (m, 4H), 7.55 (d, J=2.1 Hz, 2H), 8.21 (d, J=8.7 Hz, 2H); ¹³C NMR (75 MHz, DMSO): δ −1.6, 23.1, 26.9, 38.7, 38.9, 39.2, 39.5, 39.8, 40.1, 40.3, 48.8, 117.2, 121.5, 123.7, 123.8, 126.7, 127.4, 130.5, 133.2, 140.3, 141.7, 149.9, 183.8; HRMS (ESI−): Calcd for [M−H]−, 658.1264. found, 658.1243 (−2.1 mmu).

(3) Synthesis of SO₃iPr-Tetrahydroquinone-Si-Xanthone

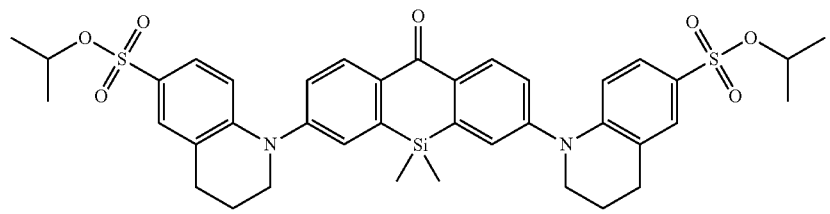 [SMILES: CC(C)OS(=O)(=O)c1ccc2c(c1)CCCN2c1ccc2c(c1)[Si](C)(C)c1cc(N3CCCc4cc(S(=O)(=O)OC(C)C)ccc43)ccc1C2=O]

SO₃H-tetrahydroquinoline-Si-xanthone (66 mg, 0.10 mmol) was dissolved in a mixed solution of 3.0 mL of CH₂Cl₂ and 1.0 mL of DMF, and then cooled to 0° C. in an argon atmosphere. Oxalyl chloride (85 μL, 0.50 mmol) was added to this solution, and the solution was stirred for two hours. Thereafter, the solvent was distilled off under reduced pressure, and the residue was dissolved in CH₂Cl₂ in an argon atmosphere. Fifteen milliliters of pyridine and 5.0 mL of i-propanol were added thereto, and the mixed solution was stirred for two hours at room temperature. The solvent was then distilled off under reduced pressure, purification was performed by column chromatography (silica gel, CH₂Cl₂/ethyl acetate=1/1), and SO₃iPr-tetrahydroquinoline-Si-xanthone (26 mg, yield 35%) was obtained.

¹H NMR (300 MHz, CDCl₃): δ 0.48 (s, 6H), 1.31 (d, J=6.6 Hz, 12H), 2.14 (tt, J=6.0 Hz, 4H), 2.93 (t, J=6.00 Hz, 4H), 3.80 (t, J=6.0 Hz, 4H), 4.75 (sep, J=6.0 Hz, 1H), 6.96 (d, J=8.7 Hz, 2H), 7.42-7.50 (m, 6H), 7.62 (d, J=1.5 Hz, 2H), 8.47 (d, J=7.8 Hz, 2H); ¹³C NMR (75 MHz, CDCl₃): δ −1.47, 22.2, 22.9, 27.5, 50.4, 115.4, 125.3, 125.4, 126.3, 126.5, 127.5, 129.3, 131.8, 136.8, 140.8, 147.5, 149.4, 185.5; HRMS (ESI+): Calcd for [M+Na]+, 767.2257. found, 767.2210 (−4.7 mmu).

(4) Synthesis of 2,6-diMe-SO₃H Tetrahydroquinoline-Si-QSY21 (Compound 4)

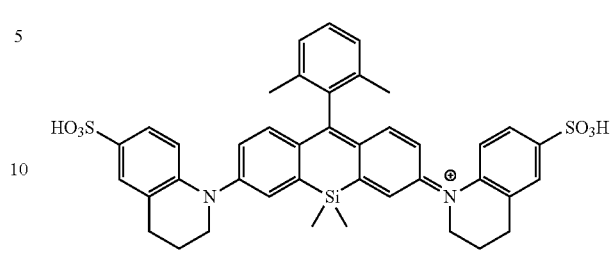

2-Bromo-m-xylene (28 mg, 0.15 mmol) was dissolved in 5 mL of dehydrated THF under argon purge, and cooled to −78° C. Thereafter, 1 M sec-BuLi THF solution (150 μL, 0.15 mmol) was added under stirring. After stirring for 30 minutes, SO₃iPr-tetrahydroquinoline-Si-xanthone (11 mg, 0.02 mmol) was dissolved in 2.0 mL of dehydrated THF, and added. After addition, the solution was returned to room temperature, and stirred for two hours. After stirring and after adding 2N HCl solution and stopping the reaction, stirring was conducted for another 15 minutes. Thereafter, following extraction by CH₂Cl₂, the organic layer was dehydrated by sodium sulfate, and distilled off under reduced pressure. The residue was dissolved in a mixed solution of 2N HCl and acetonitrile, and the solution was heat refluxed in an argon atmosphere. After the solution had returned to room temperature, it was purified by HPLC, and 2,6-diMe-SO₃H tetrahydroquinoline-Si-QSY21 (6 mg, yield 54%) was obtained.

¹H NMR (300 MHz, DMSO): δ 0.58 (s, 6H), 1.98 (br, 10H), 2.76 (t, J=6.0 Hz, 4H), 4.01 (t, J=6.6 Hz, 4H), 7.04 (d, J=9.6 Hz, 2H), 7.24 (dd, J=2.4, 9.3 Hz, 2H), 7.28 (d, J=7.8 Hz, 2H), 7.36-7.47 (m, 5H), 7.53 (s, 2H), 7.81 (d, J=2.1 Hz, 2H); HRMS (ESI−): Calcd for [M−2H]−, 747.2019. found, 747.2051 (+3.2 mmu). HPCL analysis; eluent, a 20-min linear gradient, from 1% to 100% solvent B; flow rate, 1.0 ml/min; detection wavelength, 650 nm.

Figure 5:
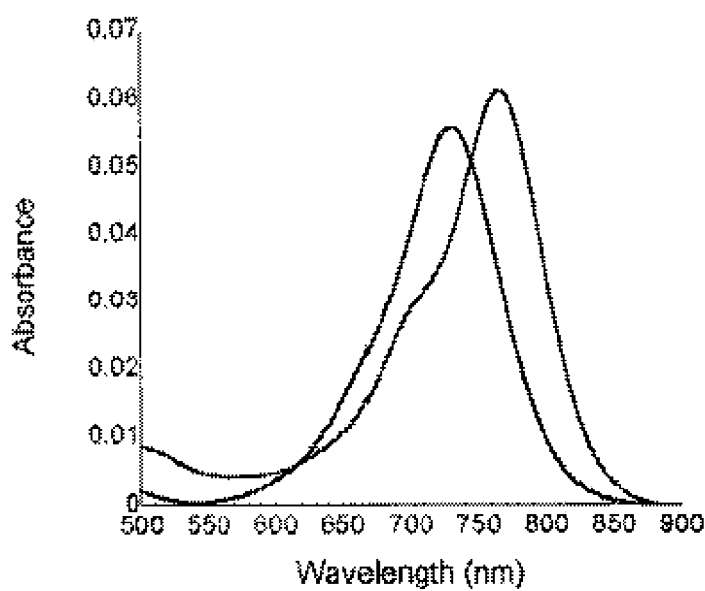

FIG. 5 shows the absorption spectra of 2,6-diMe-SO₃H indoline-Si-QSY21 (compound 1) and 2,6-diMe-SO₃H tetrahydroquinoline-Si-QSY21 (compound 4) in PBS (1% DMSO). The maximum absorption wavelength of compound 1 was 763 nm, and the maximum absorption wavelength of compound 4 was 732 nm.

Example 5

Preparation of an MMP Probe

A probe having PEG₁₁, confirmed to have a blood residence time of about six hours in vivo, bonded to the C-terminus was synthesized using compound 3, and application to animals was studied (Zhu, L., et al., Theranostics, 2011, 1, 18-27). A fluorescent group (Dy720) was also bonded to the N-terminus side in this probe. PLGVRG, a sequence thought to be recognized by a wide range of MMP, was used as the linker. A probe that employed a D-amino acid was synthesized as a control at the same time.

The construction and synthesis scheme of the MMP probe are shown below.

Construction of the MMP Probe (Si-QSY780)

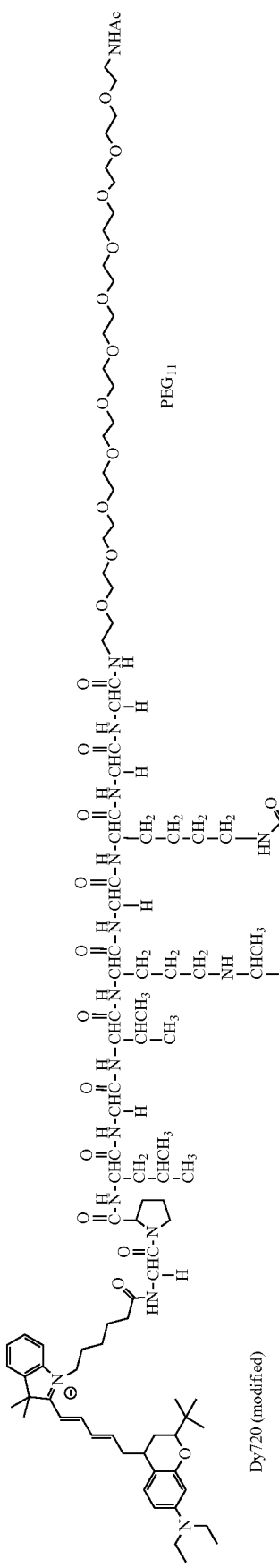

Synthesis scheme 9

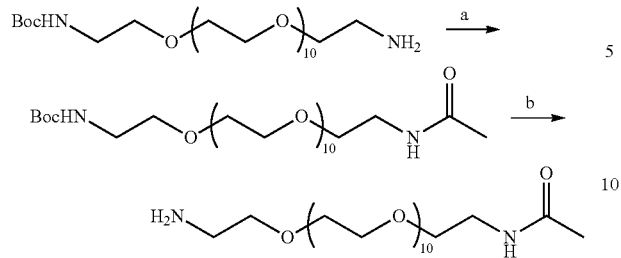

a) Ac₂O, pyridine, crude; b) TFA, CH₂Cl₂, crude.

(1) Synthesis of N-(35-Amino-3,6,9,12,15,18,21,24,27,30,33-Undecaoxapentatriacontyl)Acetamide tert-Butyl(35-amino-3,6,9,12,15,18,21,24,27,30,33-undecaoxapentatriacontyl)carbamate (1 g, 1.56 mmol) was dissolved in a mixed solution of 2 mL of acetic anhydride and 2 mL of pyridine, and stirred for two hours at room temperature. After distilling off the solvent under reduced pressure, 2 mL of trifluoroacetic acid was added, and stirred for four hours. After distilling off the solvent under reduced pressure, N-(35-amino-3,6,9,12,15,18,21,24,27,30,33-undecaoxapentatriacontyl)acetamide (1.2 g, quant) was obtained. HRMS (ESI⁺): Calcd for [M+H]⁺, 587.3755. found, 687.3708 (−4.7 mmu).

Synthesis scheme 10

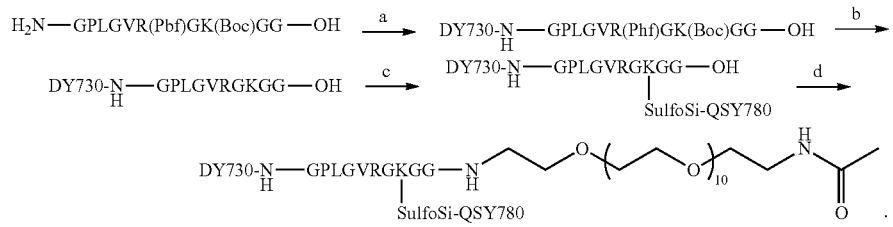

a) DY730-SE, DIEA, DMF, crude; b) TFA, triethylsilane, H₂O, crude; c) sulfoSiQSY790-SE, DIEA, DMF, y.7% (in 3 steps); d) 3, HATU, DIEA, DMF, y.51%.

(2) Synthesis of an MMP Probe

DY730-SE (20 mg) and a peptide linker (20 mg) were dissolved in 2 mL of DMF, and stirred for four hours at room temperature after adding three drops of DIEA. After distillation under reduced pressure, the product was dissolved in a mixed solvent of 2 mL of TFA, 10 μL of triethyl silane, and 10 μL of water, and stirred for two hours at room temperature. After distillation under reduced pressure, crude purification was performed by HPLC. The fraction of the target compound was freeze dried, and the solid obtained was dissolved in 1 mL of DMF. After adding sulfoSiQSYO-SE (5.2 mg) and three drops of DIEA, stirring was conducted for four hours at room temperature. After distilling off the solvent under reduced pressure, purification was performed by HPLC, and an intermediate (5 mg, yield 7%) LRMS (ESI⁺): 1120 [M]²⁺ was obtained. This was dissolved in 2 mL of DMF, and N-(35-amino-3,6,9,12,15,18,21,24,27,30,33-undecaoxapentatriacontyl)acetamide (15 mg) was added and stirred for six hours at room temperature after adding HATU (38 mg). After distilling off the solvent under reduced pressure, purification was performed by HPLC, and an MMP probe (3.2 mg, yield 51%) was obtained. LRMS (ESI⁺): 1404 [M]²⁺

Synthesis scheme 11

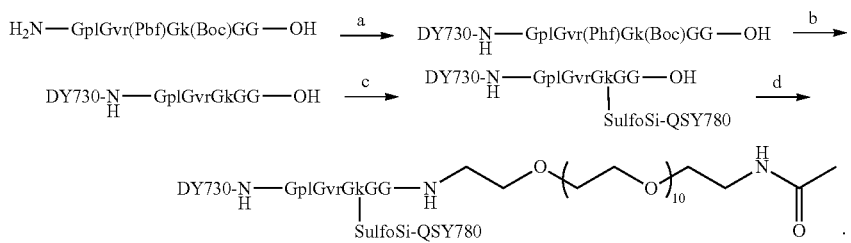

a) DY730-SE, DIEA, DMF, crude; b) TFA, triethylsilane, H₂O, crude; c) SulfoSiQSY780-SE, DIEA, DMF, y.7%(3 steps); d) PEF₁₁k HATU, DIEA, DMF, y.87%.

(3) Synthesis of a Control MMP Probe

DY730-SE (20 mg) and a control peptide linker (20 mg) were dissolved in 2 mL of DMF, and stirred for four hours at room temperature after adding three drops of DIEA. After distillation under reduced pressure, the product was dissolved in a mixed solvent of 2 mL of TFA, 10 µL of triethyl silane, and 10 µL of water, and stirred for two hours at room temperature. After distillation under reduced pressure, crude purification was performed by HPLC. The fraction of the target compound was freeze dried, and the solid obtained was dissolved in 1 mL of DMF. After adding sulfoSiQSYO-SE (5.2 mg) and three drops of DIEA, stirring was conducted for four hours at room temperature. After distilling off the solvent under reduced pressure, purification was performed by HPLC, and an intermediate (5.2 mg, yield 7%) was obtained. LRMS (ESI⁺): 995 [M]²⁺ This was dissolved in 2 mL of DMF, and N-(35-amino-3,6,9,12,15,18,21,24,27, 30,33-undecaoxapentatriacontyl)acetamide (15 mg) was added and stirred for six hours at room temperature after adding HATU (38 mg). After distilling off the solvent under reduced pressure, purification was performed by HPLC, and a control MMP probe (5.4 mg, yield 87%) was obtained. LRMS (ESI⁺): 853 [M+H]³⁺

Example 6

(1) Observation of an Enzymatic Reaction Using an MMP Probe

It was confirmed in vitro that the MMP probe (Si-QSY780) is cleaved by MMP.

Figure 6:
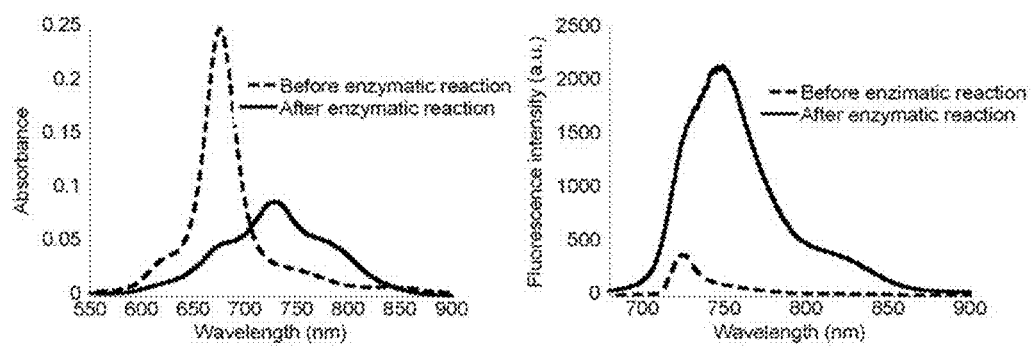
FIG. 6 Absorption spectrum and fluorescence spectrum of an MMP probe of the present invention before and after enzymatic reaction (MMP-14) of TCN buffer FIG. 7 Absorption spectrum and fluorescence spectrum of an MMP probe of the present invention before and after enzymatic reaction (MMP-9) of TCNB buffer FIG. 8 Results of measurement of DIC and fluorescence images of HT-1080 cells by an MMP probe of the present invention (1 μM) or control FIG. 9 Results of measurement of fluorescence images of HT-1080 tumor-bearing nude mice administered with an MMP probe of the present invention or control via a caudal vein FIG. 10 Changes over time in fluorescence intensity (left) and changes over time in fluorescence intensity ratio (right) of an MMP probe or control in tissue when an MMP probe of the present invention (n=5) or control (n=5) was injected intravenously into tumor tissue
Figure 7:
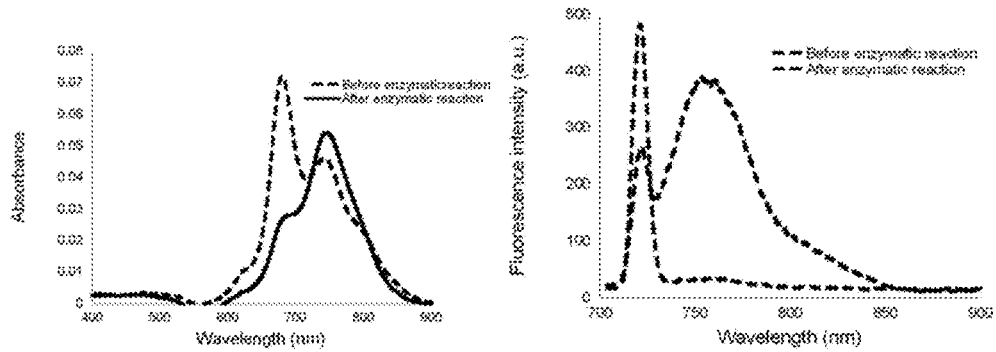

FIG. 5 (MMP-14) and FIG. 7 (MMP-9) show the absorption and fluorescence spectra of TCN buffer solution and TCNB buffer solution of the MMP probe (both containing 0.1% DMSO as cosolvent, final probe concentration: 1 µM) before and after enzymatic reaction (in each figure, the drawing on the left is the absorption spectrum, and the drawing on the right is the fluorescence spectrum). For the enzymatic reaction, an MMP-14 (MT1-MMP) catalytic domain (5 µg) (FIG. 6) or MMP-9 catalytic domain (5 µg) (FIG. 7) was added, and culture was carried out for two days. The excitation wavelength was 720 nm.

In FIGS. 6 and 7, the fluorescence intensity increased after the enzymatic reaction, showing cleavage of the probe by MMP.

(2) Imaging in a Cultured Cell System Using an MMP Probe

Imaging was conducted in cultured cells by the following protocol using an MMP probe (Si-QSY780).
Protocol
5×10⁵ cell/mL of HT-1080 cells were seeded in eight chambers and cultured for two days
After washing with PBS, it was substituted by HBSS
The probe was added to make 1 µM
Culture was carried out for six hours
Imaging was performed (IX71 (Olympus))

Figure 8:
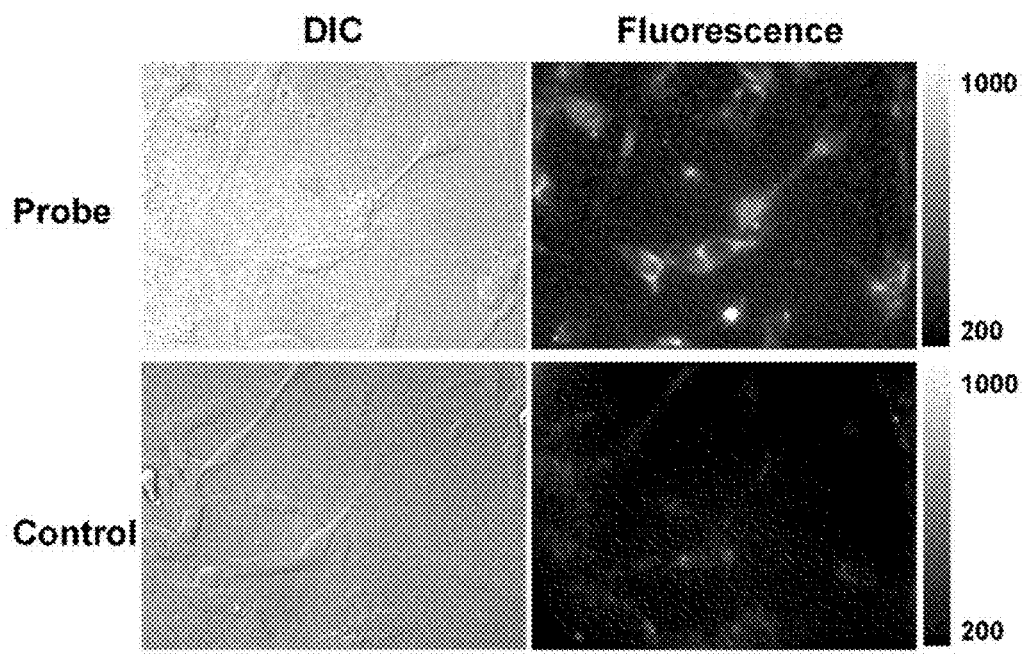

FIG. 8 shows DIC and fluorescence images of the HT-1080 cells by the MMP probe (1 µM) or control (both HBSS solution containing 0.1% DMSO as cosolvent).

As shown in FIG. 8, elevated fluorescence was observed in the extracellular fluid and within the cells, and significant differences were found from the control.

(3) Imaging in Subcutaneous Tumor Model Mice Using an MMP Probe

Figure 9:
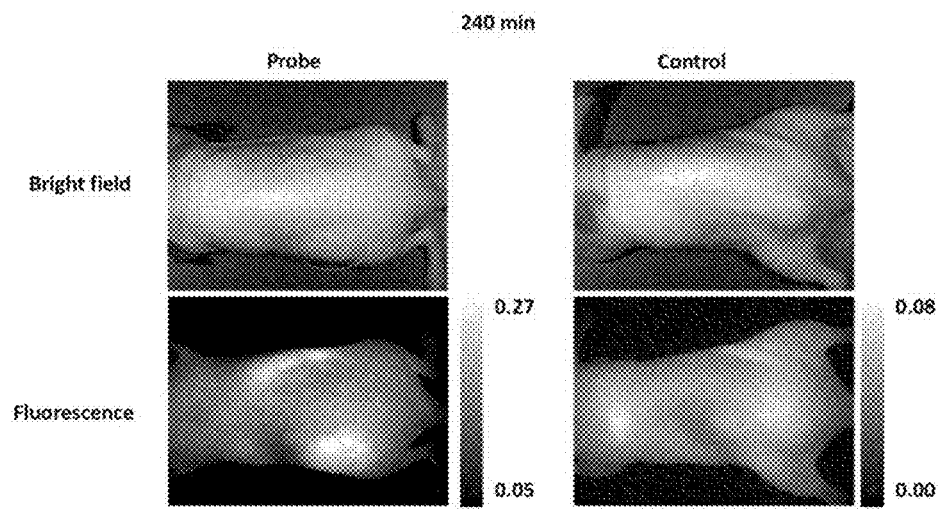

To show that the fluorescent probe of the present invention is applicable to in vivo imaging, detection of MMP activity in vivo was performed using a synthesized MMP probe (Si-QSY780). The study in subcutaneous tumor model mice, produced by subcutaneously injecting HT-1080 cells to the left lower leg as a model, was conducted based on the following protocol.
Protocol
One million cells/100 µL of HT-1080 cells were implanted beneath the skin of BALB nu/nu mice (female, 6 weeks old), and tumors were produced
100 µL of 100 µM probe was administered by injection to the caudal vein under anesthesia
Imaging was performed at each time FIG. 9 shows fluorescent images of HT-1080 tumor-bearing nude mice administered with an MMP probe (100 µM) or control (both 100 µL of PBS solution containing 0.1% DMSO as cosolvent) by caudal vein injection.

Figure 10:
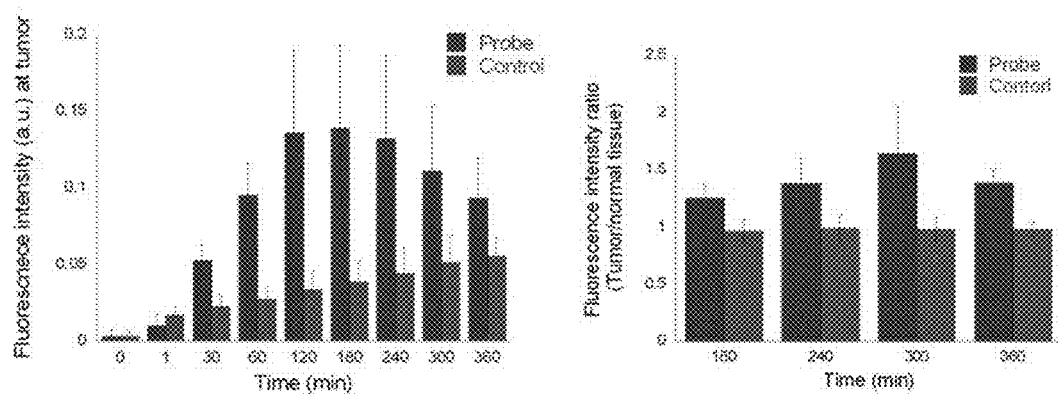

FIG. 10 shows the changes over time in the fluorescence intensity of the MMP probe or control in the tissue (left) and the changes over time in the fluorescence intensity ratio (Tumor/Muscle) of the MMP probe or control (right) when an MMP probe (n=5) or control (n=5) was injected intravenously into tumor tissue.

MMP activity in the vicinity of the tumor could be detected by intravenous injection to subcutaneous tumor model mice. In particular, the fluorescence intensity increases at the site of contact of the tumor and normal tissue. This same phenomenon is also known to have been observed previously when MMP was detected using MMPSense, and the activity of MMP, which is related to cancer infiltration and metastasis, is thought to rise at the site of contact of cancer and blood vessels.

There was a significant difference between the probe and the control, and MMP activity could be confirmed within two hours. The elevation of the fluorescence of the control is thought to be an elevation of fluorescence due to nonspecific cleavage of the probe during long-term residence and the like since the fluorescence value of the whole body was elevated rather than just that of the tumor site.

These results indicated that the compound of the present invention is in fact applicable to imaging in animals.

What is claimed is:

1. A compound represented by formula (I), or a salt thereof:

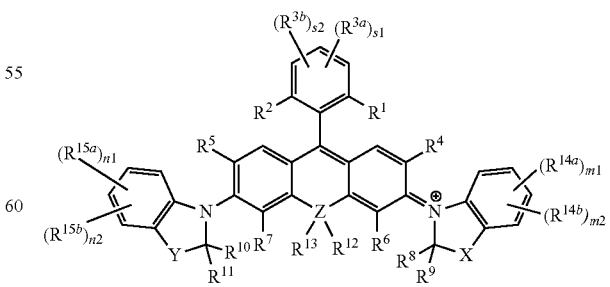

(I)

in the formula,
R¹ and R² each independently represents a C1-C6 alkyl group or a C1-C6 alkoxy group;

$R^{3a}$ represents a monovalent substituent selected from a C1-C6 alkyl group, a C1-C6 alkenyl group, a C1-C6 alkynyl group, a C1-C6 alkoxy group, a hydroxyl group, a carboxy group, a sulfonyl group, an alkoxycarbonyl group, a halogen atom, or an amino group;

$R^{3b}$ is a substituent selected from a hydroxyl group, carboxy group, sulfonyl group, alkoxycarbonyl group, or amino group;

$R^4$, $R^5$, $R^6$, and $R^7$ each independently represents a hydrogen atom, a C1-C6 alkyl group, or a halogen atom;

$R^8$, $R^9$, $R^{10}$, and $R^{11}$ each independently represents a hydrogen atom, a C1-C6 alkyl group, a hydroxyl group, or a halogen atom;

$R^{12}$ and $R^{13}$ each independently represents a C1-C6 alkyl group or an aryl group;

$R^{14a}$ and $R^{15a}$ each independently represents a C1-C6 alkyl group or a halogen atom;

$R^{14b}$ and $R^{15b}$ each independently represents an alkoxy group, an alkylamino group, a sulfone group, a phosphoric acid group, or a carboxyl group;

X and Y each independently represents $-C(R^{16})(R^{17})-$, $-C(R^{18})(R^{19})-C(R^{20})(R^{21})-$, or $-C(R^{22})=C(R^{23})-$, in which, $R^{16}$, $R^{17}$, $R^{18}$, $R^{19}$, $R^{20}$, $R^{21}$, and $R^{23}$ each independently represents a hydrogen atom, a C1-C6 alkyl group, a hydroxyl group, or a halogen atom;

Z represents a silicon atom, a germanium atom, a carbon atom, or a tin atom;

m1 and m2 each independently is an integer of 0-4, and m1+m2 is 4 or less;

n1 and n2 each independently is an integer of 0-4, and n1+n2 is 4 or less;

s1 and s2 each independently is an integer of 0-3, and s1+s2 is 3 or less.

2. The compound or salt thereof according to claim 1, wherein each of m2 and n2 is independently 1 or higher.

3. The compound or salt thereof according to claim 1 wherein s2 is 1 or higher.

4. A method for producing a compound according to claim 1, or a salt thereof, the method comprising:
(a) obtaining a compound represented by formula (III) below in which $R^4$-$R^7$, $R^{12}$, and $R^{13}$ are as defined in formula (I), by reacting a compound represented by formula (II) in which $R^4$-$R^7$, $R^{12}$, and $R^{13}$ are as defined in formula (I), with sodium nitrite and potassium iodide under acidic conditions

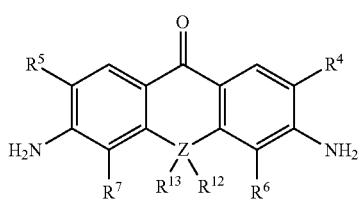
(II)

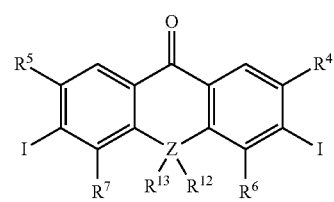
(III)

5. The method according to claim 4 comprising after (a):
(b-1) obtaining a compound represented by formula (V) in which $R^4$-$R^{13}$, $R^{14a}$, $R^{15a}$, m1, and n1 are as defined in formula (I), by reacting:
the compound of formula (III) with
a compound represented by formula (IVa) in which $R^8$, $R^9$, $R^{14a}$, X, and m1 are as defined in formula (I), and with
a compound represented by formula (IVb) in which $R^{10}$, $R^{11}$, $R^{15a}$, Y, and n1 are as defined in formula (I),
in the presence of palladium acetate and BINAP;

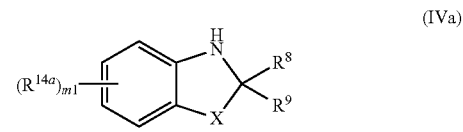
(IVa)

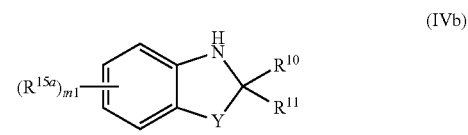
(IVb)

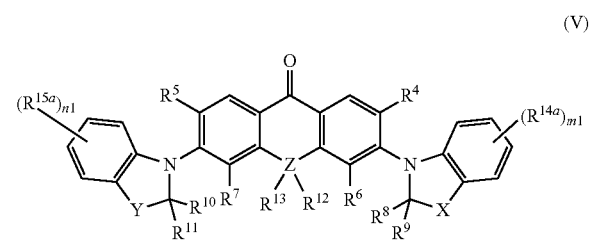
(V)

(c) obtaining a compound represented by formula (VI) in which $R^4$-$R^{14a}$, $R^{15a}$, m1, m2, n1, and n2 are as defined in formula (I), and $R^{14b}$, $R^{15b}$ are sulfone groups, by reacting the compound of formula (V) with chlorosulfonic acid;

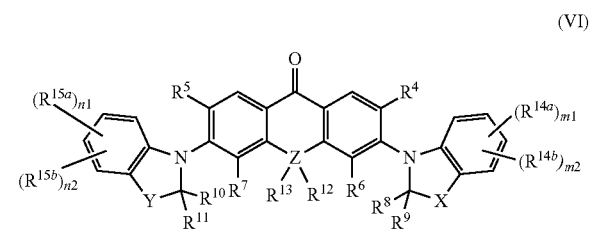
(VI)

d) obtaining a compound represented by formula (VIa) in which $R^4$-$R^{13}$, $R^{14a}$ and $R^{15a}$, m1, m2, n1, and n2 are as defined in formula (I), and ($R^{14b'}$-L) and ($R^{15b'}$-L) are groups of $R^{14b}$ and $R^{15b}$ protected by a protecting group L, respectively, by reacting the compound of formula (VI) with a protecting reagent; and

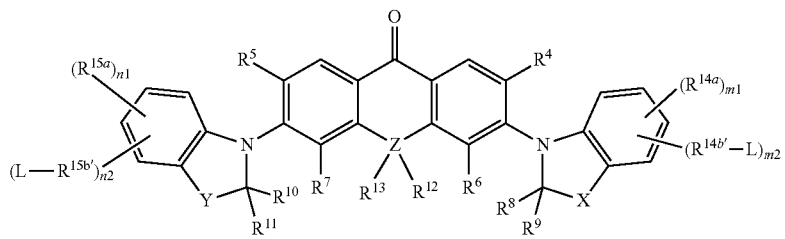

(VIa)

(e-1) obtaining a compound represented by formula (I) where, m2 and n2 are 1 or greater, and $R^{14b}$ and $R^{15b}$ are sulfone groups, by reacting:

the compound of formula (VIa) with a compound represented by formula (VII) in which $R^1$-$R^{3b}$, s1 and s2 are as defined in formula (I), and M, when present, is a protecting group of $R^{3b}$, and

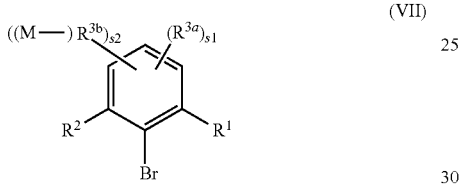

(VII)

then eliminating the protecting group L and, when M is present in formula (VII), eliminating the protecting group M.

6. The method according to claim 4 further comprising after (a):

(b-2) obtaining a compound represented by formula (Va) in which $R^4$-$R^{13}$, $R^{14a}$, $R^{15a}$, m1, and n1 are as defined in formula (I), and U and V are as defined in formulas (IVc) and (IVd), respectively, by performing a reaction comprising:

the compound of formula (III), a compound represented by formula (IVc) in which $R^8$, $R^9$, $R^{14a}$, and m1 are as defined in formula (I), and U represents $R^{14b}$ or a substituent that can be converted into $R^{14b}$ selected from a carbonyl group, a halogen group, a phosphoric acid ester group, or a sulfonic acid ester group, and a compound represented by formula (IVd) in which $R^{10}$, $R^{11}$, $R^{15a}$, and n1 are as defined in formula (I), and V represents $R^{15b}$ or a substituent that can be converted into $R^{15b}$ selected from a carbonyl group, a halogen group, a phosphoric acid ester group, or a sulfonic acid ester group, in the presence of a palladium catalyst; and

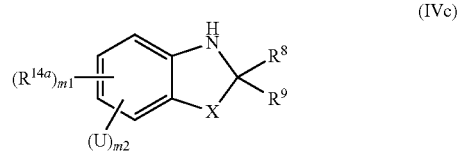

(IVc)

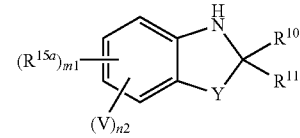

(IVd)

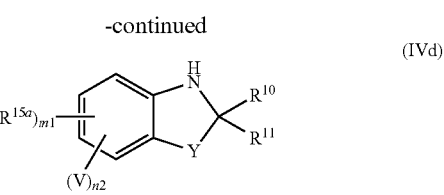

(Va)

(e-2) obtaining a compound represented by formula (I) where, m2 and n2 are 1 or higher, by reacting:

the compound of formula (Va) with a compound represented by formula (VII) in which $R^1$-$R^{3b}$, s1, and s2 are as defined in formula (I), and M, when present, is a protecting group of $R^{3b}$,

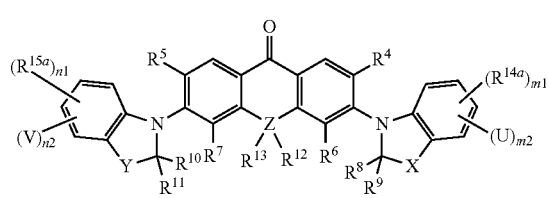

(VII)

and then eliminating the protecting group M when M is present in formula (VII), wherein when U and V, respectively, are a substituent that can be converted into $R^{14b}$ and a substituent that can be converted into $R^{15b}$, the method may comprise a step of converting U and V, respectively, into $R^{14b}$ and $R^{15b}$ before, during, or after step (e-2).

7. The method according to claim 4 comprising, after (a):

(b-1) obtaining a compound represented by formula (V) in which $R^4$-$R^{13}$, $R^{14a}$, $R^{15a}$, m1, and n1 are as defined in formula (I), by performing a reaction comprising:

the compound of formula (III), a compound represented by formula (IVa) in which $R^8$, $R^9$, $R^{14a}$, and m1 are as defined in formula (I), and

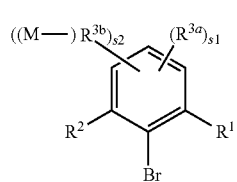

a compound represented by formula (IVb) in which $R^{10}$, $R^{11}$, $R^{15a}$, and n1 are as defined in formula (I) in the presence of a palladium catalyst; and

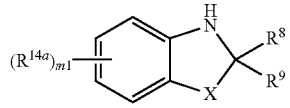

(IVa)

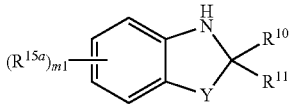

(IVb)

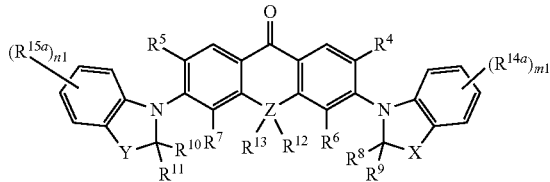

(V)

(e-3) obtaining a compound represented by formula (I) where, n1 and n2 are 0, by reacting:
the compound of formula (V) with
a compound represented by formula (VII) in which $R^1$-$R^{3b}$, s1, and s2 are as defined in formula (I), and M, when present, is a protecting group of $R^{3b}$,

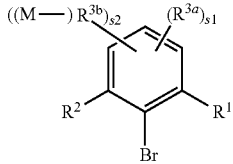

(VII)

and then eliminating the protecting group M when M is present in formula (VII).

8. A fluorescent probe capable of detecting protons, metal ions, active oxygen species, enzymes, or low-oxygen environments, or the like, wherein the fluorescent probe comprises a residue of the compound according to claim 1.

9. A fluorescent labeling reagent wherein the fluorescent labeling reagent comprises a residue of the compound according to claim 1.

10. A fluorescent probe comprising a compound having a structure wherein a residue of the compound according to claim 1 is bonded with a fluorescent dye.

11. The fluorescent probe of claim 10 wherein the compound having a structure wherein a residue of the compound is bonded directly with the fluorescent dye.

12. The fluorescent probe of claim 10 wherein the compound having a structure wherein a residue of the compound is bonded indirectly with the fluorescent dye.

13. The fluorescent probe of claim 12 wherein the compound having a structure wherein a residue of the compound is bonded indirectly with the fluorescent dye via one or more selected from the group consisting of:

an alkyl group, a polyethylene glycol group, a peptide group, a DNA group, an RNA group, a carbon atom, a nitrogen atom, a sulfur atom, or an oxygen atom.

14. The method according to claim 6 wherein the palladium catalyst is palladium acetate and the (b-2) obtaining is in the presence of BINAP.

15. The method according to claim 7 wherein the palladium catalyst is palladium acetate and the (b-1) obtaining is in the presence of BINAP.

* * * * *